(12) United States Patent
Axten et al.

(10) Patent No.: US 7,498,326 B2
(45) Date of Patent: Mar. 3, 2009

(54) COMPOUNDS

(75) Inventors: Jeffrey Michael Axten, Collegeville, PA (US); Robert A Daines, Collegeville, PA (US); David Thomas Davies, Harlow (GB); Timothy Francis Gallagher, Collegeville, PA (US); Graham Elgin Jones, Harlow (GB); William Henry Miller, Collegeville, PA (US); Neil David Pearson, Harlow (GB); Israil Pendrak, Collegeville, PA (US)

(73) Assignee: Glaxo Group Limited, Middlesex (GB)

( * ) Notice: Subject to any disclaimer, the term of this patent is extended or adjusted under 35 U.S.C. 154(b) by 353 days.

(21) Appl. No.: 10/518,655

(22) PCT Filed: Jun. 25, 2003

(86) PCT No.: PCT/EP03/06754

§ 371 (c)(1),
(2), (4) Date: Jul. 14, 2005

(87) PCT Pub. No.: WO2004/002490

PCT Pub. Date: Jan. 8, 2004

(65) Prior Publication Data

US 2006/0058287 A1 Mar. 16, 2006

Related U.S. Application Data

(60) Provisional application No. 60/391,710, filed on Jun. 26, 2002.

(51) Int. Cl.
*C07D 471/04* (2006.01)
*A61K 31/4375* (2006.01)

(52) U.S. Cl. .................................... 514/224.2; 544/48
(58) Field of Classification Search .............. 514/224.2; 544/48
See application file for complete search history.

(56) References Cited

U.S. PATENT DOCUMENTS

| | | | |
|---|---|---|---|
| 5,310,743 A | 5/1994 | Schilling et al. ............. 514/311 |
| 5,610,157 A | 3/1997 | Van Daele | |
| 5,932,590 A | 8/1999 | Ciccarone et al. ........... 514/309 |
| 6,323,217 B2 | 11/2001 | Poitevin et al. | |
| 6,403,610 B1 | 6/2002 | Malleron et al. ............. 514/314 |
| 6,602,882 B1 | 8/2003 | Davies et al. ................ 514/300 |
| 6,602,884 B2 | 8/2003 | Bacque et al. .............. 514/314 |
| 6,603,005 B2 | 8/2003 | Bacque et al. .............. 546/176 |
| 6,699,891 B1 | 3/2004 | Kawanishi et al. ........... 514/352 |
| 6,784,192 B2 | 8/2004 | Ozaki et al. ................. 514/318 |
| 6,806,277 B2 | 10/2004 | Bacque et al. .............. 514/314 |
| 6,841,562 B2 | 1/2005 | Bacque et al. .............. 514/314 |
| 6,911,442 B1 | 6/2005 | Davies et al. ............ 514/230.5 |
| 6,939,970 B2 | 9/2005 | Bourget et al. .............. 546/174 |
| 6,962,917 B2 | 11/2005 | Davies et al. ............ 514/264.1 |
| 6,989,447 B2 | 1/2006 | Markwell et al. ............ 546/152 |
| 7,001,913 B1 | 2/2006 | Davies et al. ................ 514/300 |
| 7,109,213 B2 * | 9/2006 | Daines et al. ............... 514/312 |
| 7,115,634 B2 | 10/2006 | Thurieau et al. ............. 514/320 |
| 7,141,564 B2 | 11/2006 | Brooks et al. ............. 514/224.2 |
| 7,186,730 B2 | 3/2007 | Dartois et al. ................ 514/300 |
| 7,205,408 B2 * | 4/2007 | Davies et al. ................ 546/153 |
| 7,223,776 B2 | 5/2007 | Surivet et al. ............... 514/313 |
| 7,232,832 B2 | 6/2007 | Axten et al. ................. 514/300 |
| 7,232,833 B2 | 6/2007 | Bigot et al. ................. 514/314 |
| 7,232,834 B2 | 6/2007 | Bacque et al. ............... 514/315 |
| 7,312,212 B2 * | 12/2007 | Daines et al. ............. 514/228.2 |
| 2006/0014749 A1 | 1/2006 | Davies et al. ................ 514/249 |
| 2006/0040925 A1 | 2/2006 | Davies et al. ............. 514/222.8 |
| 2006/0116512 A1 | 6/2006 | Axten et al. ................. 540/553 |
| 2006/0189601 A1 | 8/2006 | Hennessy et al. ......... 514/222.8 |
| 2006/0189604 A1 | 8/2006 | Axten et al. .............. 514/224.2 |
| 2006/0205719 A1 | 9/2006 | Hubschwerlen et al. .. 514/230.5 |
| 2007/0004710 A1 | 1/2007 | Axten et al. .............. 514/224.2 |
| 2007/0135422 A1 | 6/2007 | Brooks et al. ............ 514/224.8 |

FOREIGN PATENT DOCUMENTS

| EP | 0 445 862 A2 | 9/1991 |
|---|---|---|
| EP | 0532456 | 3/1993 |
| EP | 0643057 | 3/1995 |
| FR | 2815031 | 4/2002 |

(Continued)

OTHER PUBLICATIONS

C. Wermuth, "Molecular Variations Based on Isosteric Replacements", *The Practice of Medicinal Chemistry*, pp. 203-237 (1996).

(Continued)

*Primary Examiner*—Kahsay T Habte
(74) *Attorney, Agent, or Firm*—Lorretta J. Sauermelch; Mary E. McCarthy; Charles M. Kinzig

(57) ABSTRACT

Piperidine derivatives and pharmaceutically acceptable derivatives thereof useful in methods of treatment of bacterial infections in mammals, particularly in man. The piperidine derivatives include compounds of formula (I):

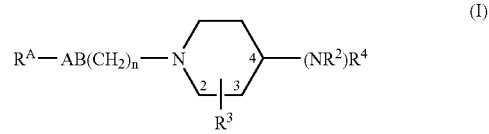

wherein $R^A$, AB, n, $R^3$, $R^2$ and $R^4$ are defined herein. For example, $R^A$ is an optionally substituted bicyclic carbocyclic or heterocyclic ring system, and $R^4$ is a group U-$R^5$ in which $R^5$ is an optionally substituted bicyclic heterocyclic ring system as defined herein (e.g. optionally substituted pyrido [3,2,-b][1,4] thiazin-yl).

16 Claims, No Drawings

FOREIGN PATENT DOCUMENTS

| | | |
|---|---|---|
| GB | 1 375 836 | 11/1974 |
| WO | WO94/10174 | 5/1994 |
| WO | WO94/27967 | 12/1994 |
| WO | WO96/26205 | 8/1996 |
| WO | WO97/17957 | 5/1997 |
| WO | WO97/38665 | 10/1997 |
| WO | WO99/28314 | 6/1999 |
| WO | WO99/37304 | 7/1999 |
| WO | WO99/37635 | 7/1999 |
| WO | WO00/21948 | 4/2000 |
| WO | WO00/21952 | 4/2000 |
| WO | WO00/43383 | 7/2000 |
| WO | WO00/78748 A1 | 12/2000 |
| WO | WO01/07432 A2 | 2/2001 |
| WO | WO01/07433 A2 | 2/2001 |
| WO | WO01/07436 | 2/2001 |
| WO | WO01/14333 | 3/2001 |
| WO | WO01/19788 | 3/2001 |
| WO | WO01/25227 A2 | 4/2001 |
| WO | WO01/37826 | 5/2001 |
| WO | WO01/44191 | 6/2001 |
| WO | WO01/53288 | 7/2001 |
| WO | WO01/64642 | 9/2001 |
| WO | WO01/64643 | 9/2001 |
| WO | WO01/70673 | 9/2001 |
| WO | WO01/72712 | 10/2001 |
| WO | WO01/87839 | 11/2001 |
| WO | WO 02/08224 A1 | 1/2002 |
| WO | WO02/24649 | 3/2002 |
| WO | WO02/24684 A1 | 3/2002 |
| WO | WO02/40474 | 5/2002 |
| WO | WO02/50040 A1 | 6/2002 |
| WO | WO02/50061 A1 | 6/2002 |
| WO | WO 02/056882 A1 | 7/2002 |
| WO | WO02/072572 A1 | 9/2002 |
| WO | WO02/083641 | 10/2002 |
| WO | WO02/096907 A1 | 12/2002 |
| WO | WO03/010138 A2 | 2/2003 |
| WO | WO 03/064421 A1 | 8/2003 |
| WO | WO 03/064431 A2 | 8/2003 |
| WO | WO03/087098 | 10/2003 |
| WO | WO2004/002992 A1 | 1/2004 |
| WO | WO2004/011454 A2 | 2/2004 |
| WO | WO2004/014361 A1 | 2/2004 |
| WO | WO2004/024712 A1 | 3/2004 |
| WO | WO2004/024713 A1 | 3/2004 |
| WO | WO2004/035569 | 4/2004 |
| WO | WO2004/041210 A2 | 5/2004 |
| WO | WO2004/050036 A2 | 6/2004 |
| WO | WO2004/058144 A2 | 7/2004 |
| WO | WO2004/060886 | 7/2004 |
| WO | WO2004/087145 A2 | 10/2004 |
| WO | WO2004/087647 | 10/2004 |
| WO | WO2004/089947 | 10/2004 |
| WO | WO2004/096982 A2 | 11/2004 |

OTHER PUBLICATIONS

Derwent Abstract 2002-397066/43 (Oct. 11, 2000)—Heterocyclic and carbocyclic compounds have serotoninergic transmission modifying properties for the treatment of centeral and peripheral nervous disorders; Fillion et al. (FR2815031).

* cited by examiner

COMPOUNDS

This application is a national stage entry of PCT/EP2003/006754, filed Jun. 25, 2003 which claims the benefit of U.S. Provisional Application No. 60/391,710, filed Jun. 26, 2002.

This invention relates to novel compounds, compositions containing them and their use as antibacterials.

WO99/37635, WO00/21948, WO00/21952, WO00/43383, WO00/78748, WO01/07432, WO01/07433, WO02/08224, WO02/24684, WO02/50040, WO02/56882, WO02/96907, PCT/EP02/05708, WO03010138, WO01/25227, WO0240474 and WO0207572 disclose cyclohexane, piperidine and piperazine derivatives having antibacterial activity.

This invention provides a compound of formula (I) or a pharmaceutically acceptable derivative thereof:

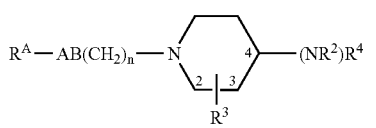

(I)

wherein:

$R^A$ is an optionally substituted bicyclic carbocyclic or heterocyclic ring system of structure:

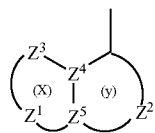

containing 0-3 heteroatoms in each ring in which:
at least one of rings (x) and (y) is aromatic;
one of $Z^4$ and $Z^5$ is C or N and the other is C;
$Z^3$ is N, $NR^{13}$, O, $S(O)_x$, CO, $CR^1$ or $CR^1R^{1a}$;
$Z^1$ and $Z^2$ are independently a 2 or 3 atom linker group each atom of which is independently selected from N, $NR^{13}$, O, $S(O)_x$, CO, $CR^1$ and $CR^1R^{1a}$;
such that each ring is independently substituted with 0-3 groups $R^1$ and/or $R^{1a}$;
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;
$R^1$ and $R^{1a}$ are independently hydrogen; hydroxy; ($C_{1-6}$) alkoxy optionally substituted by ($C_{1-6}$)alkoxy, amino, piperidyl, guanidino or amidino any of which is optionally N-substituted by one or two ($C_{1-6}$)alkyl, acyl or ($C_{1-6}$) alkylsulphonyl groups, $CONH_2$, hydroxy, ($C_{1-6}$)alkylthio, heterocyclylthio, heterocyclyloxy, arylthio, aryloxy, acylthio, acyloxy or ($C_{1-6}$)alkylsulphonyloxy; ($C_{1-6}$) alkoxy-substituted($C_{1-6}$)alkyl; hydroxy ($C_{1-6}$)alkyl; halogen; ($C_{1-6}$)alkyl; ($C_{1-6}$)alkylthio; trifluoromethyl; trifluoromethoxy; cyano; carboxy; nitro; azido; acyl; acyloxy; acylthio; ($C_{1-6}$)alkylsulphonyl; ($C_{1-6}$)alkylsulphoxide; arylsulphonyl; arylsulphoxide or an amino, piperidyl, guanidino or amidino group optionally N-substituted by one or more ($C_{1-6}$)alkyl, acyl or ($C_{1-6}$)alkylsulphonyl groups, or when $Z^3$ and the adjacent atom are $CR^1$ and $CR^{1a}$, $R^1$ and $R^{1a}$ may together represent ($C_{1-2}$)alkylenedioxy;

provided that $R^1$ and $R^{1a}$ on the same carbon atom are not both optionally substituted hydroxy or amino;

provided that
(i) when $R^A$ is optionally substituted quinolin-4-yl:
  it is unsubstituted in the 6-position; or
  it is substituted by at least one hydroxy ($C_{1-6}$)alkyl, cyano or carboxy group at the 2-, 5-, 6-, 7- or 8-position; or
  it is substituted by at least one trifluoromethoxy group; or
  $R^1$ and $R^{1a}$ together represent ($C_{1-2}$)alkylenedioxy;
(ii) when $R^A$ is optionally substituted quinazolin-4-yl, cinnolin-4-yl, 1,5-naphthyridin-4-yl, 1,7-naphthyridin-4-yl or 1,8-naphthyridin-4-yl:
  it is substituted by at least one hydroxy ($C_{1-6}$)alkyl, cyano or carboxy group at the 2-, 5-, 6-, 7- or 8-position as available; or
  it is substituted by at least one trifluoromethoxy group; or
  $R^1$ and $R^{1a}$ together represent ($C_{1-2}$)alkylenedioxy;

$R^2$ is hydrogen, or ($C_{1-4}$)alkyl or ($C_{2-4}$)alkenyl optionally substituted with 1 to 3 groups selected from:
amino optionally substituted by one or two ($C_{1-4}$)alkyl groups; carboxy; ($C_{1-4}$)alkoxycarbonyl; ($C_{1-4}$)alkylcarbonyl; ($C_{2-4}$)alkenyloxycarbonyl; ($C_{2-4}$)alkenylcarbonyl; aminocarbonyl wherein the amino group is optionally substituted by hydroxy, ($C_{1-4}$)alkyl, hydroxy($C_{1-4}$)alkyl, aminocarbonyl($C_{1-4}$)alkyl, ($C_{2-4}$)alkenyl, ($C_{1-4}$)alkylsulphonyl, trifluoromethylsulphonyl, ($C_{2-4}$)alkenylsulphonyl, ($C_{1-4}$)alkoxycarbonyl, ($C_{1-4}$)alkylcarbonyl, ($C_{2-4}$)alkenyloxycarbonyl or ($C_{2-4}$)alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; ($C_{1-4}$)alkylthio; trifluoromethyl; hydroxy optionally substituted by ($C_{1-4}$)alkyl, ($C_{2-4}$)alkenyl, ($C_{1-4}$)alkoxycarbonyl, ($C_{1-4}$)alkylcarbonyl, ($C_{2-4}$)alkenyloxycarbonyl, ($C_{2-4}$)alkenylcarbonyl; oxo; ($C_{1-4}$)alkylsulphonyl; ($C_{2-4}$)alkenylsulphonyl; or ($C_{1-4}$)aminosulphonyl wherein the amino group is optionally substituted by ($C_{1-4}$)alkyl or ($C_{2-4}$)alkenyl;

$R^3$ is hydrogen; or
$R^3$ is in the 2-, 3- or 4-position and is:
trifluoromethyl; carboxy; ($C_{1-6}$)alkoxycarbonyl; ($C_{2-6}$)alkenyloxycarbonyl; aminocarbonyl wherein the amino group is optionally substituted by hydroxy, ($C_{1-6}$)alkyl, hydroxy ($C_{1-6}$)alkyl, aminocarbonyl($C_{1-6}$)alkyl, ($C_{2-6}$)alkenyl, ($C_{1-6}$) alkylsulphonyl, trifluoromethylsulphonyl, ($C_{2-6}$)alkenylsulphonyl, ($C_{1-6}$)alkoxycarbonyl, ($C_{1-6}$) alkylcarbonyl, ($C_{2-6}$)alkenyloxycarbonyl or ($C_{2-6}$) alkenylcarbonyl and optionally further substituted by ($C_{1-6}$) alkyl, hydroxy($C_{1-6}$)alkyl, aminocarbonyl($C_{1-6}$)alkyl or ($C_{2-6}$)alkenyl; cyano; tetrazolyl; 2-oxo-oxazolidinyl optionally substituted by $R^{10}$; 3-hydroxy-3-cyclobutene-1, 2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or ($C_{1-4}$)alkyl or ethenyl optionally substituted with any of the substituents listed above for $R^3$ and/or 0 to 2 groups $R^{12}$ independently selected from:
halogen; ($C_{1-6}$)alkylthio; trifluoromethyl; ($C_{1-6}$)alkoxycarbonyl; ($C_{1-6}$)alkylcarbonyl; ($C_{2-6}$)alkenyloxycarbonyl; ($C_{2-6}$)alkenylcarbonyl; hydroxy optionally substituted by ($C_{1-6}$)alkyl, ($C_{2-6}$)alkenyl, ($C_{1-6}$)alkoxycarbonyl, ($C_{1-6}$)alkylcarbonyl, ($C_{2-6}$)alkenyloxycarbonyl, ($C_{2-6}$)alkenylcarbonyl or aminocarbonyl wherein the amino group is optionally substituted by ($C_{1-6}$)alkyl, ($C_{2-6}$)alkenyl, ($C_{1-6}$)alkylcarbonyl or (C$_{2-6}$)alkenylcarbonyl; amino optionally mono- or disubstituted by (C$_{1-6}$)alkoxycarbonyl, (C$_{1-6}$)alkylcarbonyl, (C$_{2-6}$)alkenyloxycarbonyl, (C$_{2-6}$)alkenylcarbonyl, (C$_{1-6}$)alkyl, (C$_{2-6}$)alkenyl, (C$_{1-6}$)alkylsulphonyl, (C$_{2-6}$)alkenylsulphonyl or aminocarbonyl wherein the amino group is optionally substituted by (C$_{1-6}$)alkyl or (C$_{2-6}$)alkenyl; aminocarbonyl wherein the amino group is optionally substituted by (C$_{1-6}$)alkyl, hydroxy(C$_{1-6}$)alkyl, aminocarbonyl(C$_{1-6}$)alkyl, (C$_{2-6}$)alkenyl, (C$_{1-6}$)alkoxycarbonyl, (C$_{1-6}$)alkylcarbonyl, (C$_{2-6}$)alkenyloxycarbonyl or (C$_{2-6}$)alkenylcarbonyl and optionally further substituted by (C$_{1-6}$)alkyl, hydroxy (C$_{1-6}$)alkyl, aminocarbonyl(C$_{1-6}$)alkyl or (C$_{2-6}$)alkenyl; oxo; (C$_{1-6}$)alkylsulphonyl; (C$_{2-6}$)alkenylsulphonyl; or (C$_{1-6}$)aminosulphonyl wherein the amino group is optionally substituted by (C$_{1-6}$)alkyl or (C$_{2-6}$)alkenyl; or $R^3$ is in the 2-position and is oxo; or $R^3$ is in the 3-position and is fluorine, amino optionally substituted by a group selected from hydroxy, (C$_{1-6}$)alkylsulphonyl, trifluoromethylsulphonyl, (C$_{2-6}$)alkenylsulphonyl, (C$_{1-6}$)alkylcarbonyl, (C$_{2-6}$)alkenylcarbonyl, (C$_{1-6}$)alkoxycarbonyl, (C$_{2-6}$)alkenyloxycarbonyl, (C$_{1-6}$)alkyl and (C$_{2-6}$)alkenyl, wherein a (C$_{1-6}$)alkyl or (C$_{2-6}$)alkenyl moiety may be optionally substituted with up to 2 groups $R^{12}$, or hydroxy optionally substituted as described above for $R^{12}$ hydroxy;

in addition when $R^3$ is disubstituted with a hydroxy or amino containing substituent and carboxy containing substituent these may together form a cyclic ester or amide linkage, respectively;

$R^4$ is a group -U-$R^5$ where

U is selected from CO, SO$_2$ and CH$_2$ and $R^5$ is an optionally substituted bicyclic carbocyclic or heterocyclic ring system (A):

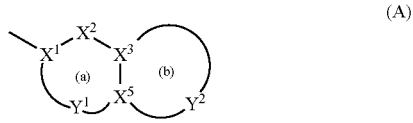

containing up to four heteroatoms in each ring in which
at least one of rings (a) and (b) is aromatic;

$X^1$ is C or N when part of an aromatic ring, or $CR^{14}$ when part of a non-aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;

$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;

each of $R^{14}$ and $R^{15}$ is independently selected from: H; (C$_{1-4}$)alkylthio; halo; carboxy(C$_{1-4}$)alkyl; halo(C$_{1-4}$)alkoxy; halo(C$_{1-4}$)alkyl; (C$_{1-4}$)alkyl; (C$_{2-4}$)alkenyl; (C$_{1-4}$) alkoxycarbonyl; formyl; (C$_{1-4}$)alkylcarbonyl; (C$_{2-4}$)alkenyloxycarbonyl; (C$_{2-4}$)alkenylcarbonyl; (C$_{1-4}$) alkylcarbonyloxy; (C$_{1-4}$)alkoxycarbonyl(C$_{1-4}$) alkyl; hydroxy; hydroxy(C$_{1-4}$)alkyl; mercapto(C$_{1-4}$)alkyl; (C$_{1-4}$)alkoxy; nitro; cyano; carboxy; amino or aminocarbonyl optionally substituted as for corresponding substituents in $R^3$; (C$_{1-4}$)alkylsulphonyl; (C$_{2-4}$)alkenylsulphonyl; or aminosulphonyl wherein the amino group is optionally mono- or di-substituted by (C$_{1-4}$)alkyl or (C$_{2-4}$) alkenyl; aryl; aryl(C$_{1-4}$)alkyl; aryl(C$_{1-4}$)alkoxy or $R^{14}$ and $R^{15}$ may together represent oxo;

each $R^{13}$ is independently H; trifluoromethyl; (C$_{1-4}$)alkyl optionally substituted by hydroxy, (C$_{1-6}$)alkoxy, (C$_{1-6}$) alkylthio, halo or trifluoromethyl; (C$_{2-4}$)alkenyl; aryl; aryl (C$_{1-4}$)alkyl; arylcarbonyl; heteroarylcarbonyl; (C$_{1-4}$) alkoxycarbonyl; (C$_{1-4}$)alkylcarbonyl; formyl; (C$_{1-6}$)alkylsulphonyl; or aminocarbonyl wherein the amino group is optionally substituted by (C$_{1-4}$)alkoxycarbonyl, (C$_{1-4}$)alkylcarbonyl, (C$_{2-4}$)alkenyloxycarbonyl, (C$_{2-4}$)alkenylcarbonyl, (C$_{1-4}$)alkyl or (C$_{2-4}$)alkenyl and optionally further substituted by (C$_{1-4}$)alkyl or (C$_{2-4}$) alkenyl;

each x is independently 0, 1 or 2 n is 0 and AB is $NR^{11}CO$, $CO-CR^8R^9$, $CR^6R^7-CO$, $NHR^{11}SO_2$, $CR^6R^7-SO_2$ or $CR^6R^7-CR^8R^9$, provided that $R^8$ and $R^9$ are not optionally substituted hydroxy or amino and $R^6$ and $R^8$ do not represent a bond:

or n is 1 and AB is $NR^{11}CO$, $CO-CR^8R^9$, $CR^6R^7-CO$, $NR^{11}SO_2$, $CONR^{11}$, $CR^6R^7-CR^8R^9$, $O-CR^8R^9$ or $NR^{11}-CR^8R^9$;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; (C$_{1-6}$)alkoxy; (C$_{1-6}$)alkylthio; halo; trifluoromethyl; azido; (C$_{1-6}$)alkyl; (C$_{2-6}$)alkenyl; (C$_{1-6}$)alkoxycarbonyl; (C$_{1-6}$) alkylcarbonyl; (C$_{2-6}$)alkenyloxycarbonyl; (C$_{2-6}$)alkenylcarbonyl; hydroxy, amino or aminocarbonyl optionally substituted as for corresponding substituents in $R^3$; (C$_{1-6}$) alkylsulphonyl; (C$_{2-6}$)alkenylsulphonyl; or (C$_{1-6}$)aminosulphonyl wherein the amino group is optionally substituted by (C$_{1-6}$)alkyl or (C$_{2-6}$)alkenyl;

or $R^6$ and $R^8$ together represent a bond and $R^7$ and $R^9$ are as above defined;

$R^{10}$ is selected from (C$_{1-4}$)alkyl; (C$_{2-4}$)alkenyl and aryl any of which may be optionally substituted by a group $R^{12}$ as defined above; carboxy; aminocarbonyl wherein the amino group is optionally substituted by hydroxy, (C$_{1-6}$)alkyl, (C$_{2-6}$)alkenyl, (C$_{1-6}$)alkylsulphonyl, trifluoromethylsulphonyl, (C$_{2-6}$)alkenylsulphonyl, (C$_{1-6}$)alkoxycarbonyl, (C$_{1-6}$)alkylcarbonyl, (C$_{2-6}$)alkenyloxycarbonyl or (C$_{2-6}$) alkenylcarbonyl and optionally further substituted by (C$_{1-6}$) alkyl or (C$_{2-6}$)alkenyl; and $R^{11}$ is hydrogen; trifluoromethyl, (C$_{1-6}$)alkyl; (C$_{2-6}$)alkenyl; (C$_{1-6}$)alkoxycarbonyl; (C$_{1-6}$)alkylcarbonyl; or aminocarbonyl wherein the amino group is optionally substituted by (C$_{1-6}$)alkoxycarbonyl, (C$_{1-6}$)alkylcarbonyl, (C$_{2-6}$)alkenyloxycarbonyl, (C$_{2-6}$)alkenylcarbonyl, (C$_{1-6}$)alkyl or (C$_{2-6}$) alkenyl and optionally further substituted by (C$_{1-6}$)alkyl or (C$_{2-6}$)alkenyl;

or where one of $R^3$ and $R^6$, $R^7$, $R^8$ or $R^9$ contains a carboxy group and the other contains a hydroxy or amino group they may together form a cyclic ester or amide linkage.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

In one aspect $R^4$ is not indole or benzofuran.

Preferably $Z^2$ is three atoms long.

Preferably $Z^4$ and $Z^5$ are both carbon.

Preferably $Z^1$ is three atoms long with carbon joined to $Z^3$ and with $R^1$ on the carbon atom joined to $Z^3$.

In one preferred aspect, $R^4$ is aromatic and ring (y) is fused benzene. Preferably (x) is 6-membered containing one or two nitrogen atoms, the remainder being carbon. Most preferably $Z^3$ is nitrogen and the remainder are carbon or $Z^1$ is =CH—CH=N— (N attached to $Z^5$).

In another preferred aspect, ring (y) is fused pyridin-4-yl ($Z^2$ is three atoms long, the atom attached to $Z^5$ in $Z^2$ is nitrogen and the remainder and $Z^4$ and $Z^5$ are carbon), $Z^1$ is two or three atoms long and $Z^3$ is a heteroatom such as O or S.

Suitable examples of rings $R^4$ include optionally substituted isoquinolin-5-yl, quinolin-8-yl, thieno[3,2-b]pyridin-7-yl, 2,3-dihydro-[1,4]dioxino[2,3-b]pyridin-8-yl, quinoxalin-5-yl, isoquinolin-8-yl, [1,6]-naphthyridin-4-yl, 1,2,3,4-tetrahydroquinoxalin-5-yl and 1,2-dihydroisoquinoline-8-yl. Most preferably $R^4$ is optionally 2-substituted-quinolin-8-yl or optionally 3-substituted-quinoxalin-5-yl.

$R^{13}$ in rings (x) and (y) is preferably H or $(C_{1-6})$alkyl.

When $R^1$ or $R^{1a}$ is substituted alkoxy it is preferably $(C_{2-6})$ alkoxy substituted by optionally N-substituted amino, or $(C_{1-6})$ alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy or 2-aminocarbonylprop-2-oxy.

Preferably $R^1$ and $R^{1a}$ are independently hydrogen, $(C_{1-4})$ alkoxy, $(C_{1-4})$alkylthio, $(C_{1-4})$alkyl, amino$(C_{3-5})$akyloxy, nitro, cyano, carboxy, hydroxymethyl or halogen; more preferably hydrogen, methoxy, methyl, cyano, halogen or amino $(C_{3-5})$alkyloxy. Ring $R^4$ is preferably substituted by one group $R^1$. Most preferably $R^1$ is H, methoxy, methyl, cyano or halogen and $R^{1a}$ is H. Halogen is preferably chloro or fluoro.

Preferably n is 0.

$R^2$ is preferably hydrogen; $(C_{1-4})$alkyl substituted with carboxy, optionally substituted hydroxy, optionally substituted aminocarbonyl, optionally substituted amino or $(C_{1-4})$ alkoxycarbonyl; or $(C_{2-4})$alkenyl substituted with $(C_{1-4})$ alkoxycarbonyl or carboxy. More preferred groups for $R^2$ are hydrogen, carboxymethyl, hydroxyethyl, aminocarbonylmethyl, ethoxycarbonylmethyl, ethoxycarbonylalkyl and carboxyalkyl, most preferably hydrogen.

Preferred examples of $R^3$ include hydrogen; optionally substituted hydroxy; optionally substituted amino; halogen; $(C_{1-4})$alkoxycarbonyl; $(C_{1-4})$ alkyl; ethenyl; optionally substituted 1-hydroxy-$(C_{1-4})$ alkyl; optionally substituted aminocarbonyl; carboxy$(C_{1-4})$alkyl; optionally substituted aminocarbonyl$(C_{1-4})$alkyl; cyano$(C_{1-4})$alkyl; optionally substituted 2-oxo-oxazolidinyl and optionally substituted 2-oxo-oxazolidinyl$(C_{1-4}$alkyl). More preferred $R^3$ groups are hydrogen; CONH$_2$; 1-hydroxyalkyl e.g. CH$_2$OH, CH(OH) CH$_2$CN; CH$_2$CO$_2$H; CH$_2$CONH$_2$; CONHCH$_2$CONH$_2$; 1,2-dihydroxyalkyl e.g. CH(OH)CH$_2$OH; CH$_2$CN; 2-oxo-oxazolidin-5-yl, 2-oxo-oxazolidin-5-yl($C_{1-4}$alkyl); optionally substituted hydroxy; optionally substituted amino; and halogen, in particular fluoro. Most preferably $R^3$ is hydrogen, hydroxy or fluoro.

$R^3$ is preferably in the 3- or 4-position.

When $R^3$ is in the 3-position, preferably it is trans to (NR$^2$) $R^4$ and has R stereochemistry or is cis to NR$^2$R$^4$ and has S stereochemistry.

When $R^3$ and $R^6$, $R^7$, $R^8$ or $R^9$ together form a cyclic ester or amide linkage, it is preferred that the resulting ring is 5-7 membered. It is further preferred that the group A or B which does not form the ester or amide linkage is CH$_2$.

Preferably n=0.

In one aspect, CR$^6$R$^7$ is CH$_2$, CHOH, CH(NH$_2$), C(Me) (OH) or CH(Me) and CR$^8$R$^9$ is CH$_2$.

When A is CH(OH) the R-stereochemistry is preferred.

Preferably A is NH, NCH$_3$, CH$_2$, CHOH, CH(NH$_2$), C(Me)(OH) or CH(Me).

Preferably B is CH$_2$ or CO.

Preferably A-B is CH$_2$—CH$_2$, CHOH—CH$_2$, NR$^{11}$—CH$_2$ or NR$^{11}$—CO.

Particularly preferred are those compounds where n=0, A and B are both CH$_2$, A is NH and B is CO, or A is CHOH and B is CH$_2$, when more preferably A is the R-isomer of CHOH.

Preferably $R^{11}$ is hydrogen or $(C_{1-4})$alkyl e.g. methyl, more preferably hydrogen.

U is most preferably CH$_2$.

Preferably $R^5$ is an aromatic heterocyclic ring (A) having 8-11 ring atoms including 2-4 heteroatoms of which at least one is N or NR$^{13}$ in which preferably Y$^2$ contains 2-3 heteroatoms, one of which is S and 1-2 are N, with one N bonded to $X^3$.

Alternatively and preferably the heterocyclic ring (A) has ring (a) aromatic selected from optionally substituted benzo and pyrido and ring (b) non aromatic and Y$^2$ has 3-5 atoms, more preferably 4 atoms, including a heteroatom bonded to X$^5$ selected from O, S or NR$^{13}$, where R$^{13}$ is other than hydrogen, and NHCO bonded via N to X$^3$, or O bonded to X$^3$. The ring (a) preferably contains aromatic nitrogen, and more preferably ring (a) is pyridine. Examples of rings (A) include optionally substituted:

(a) and (b) aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2-yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl (a) is non aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, (b) is non aromatic 1,1,3-trioxo-1,2,3,4-tetrahydro1 $1^6$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 6-oxo-6,7-dihydro-5H-8-thia-1,2,5-triaza-naphthalen-3-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl.

$R^{13}$ is preferably H if in ring (a) or in addition $(C_{1-4})$alkyl such as methyl or isopropyl when in ring (b). More preferably, in ring (b) $R^{13}$ is H when $NR^{13}$ is bonded to $X^3$ and $(C_{1-4})$alkyl when $NR^{13}$ is bonded to $X^5$.

$R^{14}$ and $R^{15}$ are preferably independently selected from hydrogen, halo, hydroxy, $(C_{1-4})$ alkyl, $(C_{1-4})$alkoxy, trifluoromethoxy, nitro, cyano, aryl$(C_{1-4})$alkoxy and $(C_{1-4})$alkylsulphonyl. More preferably $R^{15}$ is hydrogen.

More preferably each $R^{14}$ is selected from hydrogen, chloro, fluoro, hydroxy, methyl, methoxy, trifluoromethoxy, benzyloxy, nitro, cyano and methylsulphonyl. Most preferably $R^{14}$ is selected from hydrogen, fluorine or nitro.

Most preferably $R^{14}$ and $R^{15}$ are each H.

Most preferred groups $R^5$ include:

[1,2,3]thiadiazolo[5,4-b]pyridin-6-yl
1H-Pyrrolo[2,3-b]pyridin-2-yl
2,3-Dihydro-[1,4]dioxino[2,3-b]pyridin-6-yl
2,3-Dihydro-[1,4]dioxino[2,3-b]pyridin-7-yl
2,3-Dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-Methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-Hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl especially 3-oxo-3,4-dihydro-2H-pyrido[3,2-b][1,4]oxazin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2,3-dihydro-[1,4]dioxino[2,3-c]pyridin-7-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.
Haloalkyl moieties include 1-3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl$(C_{1-4})$alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautomeric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl $(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy The term "acyl" includes formyl and $(C_{1-6})$alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the abovementioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

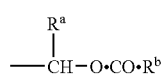

(i)

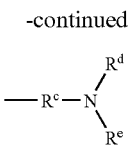

(ii)

—CH$_2$—OR$^f$ (iii)

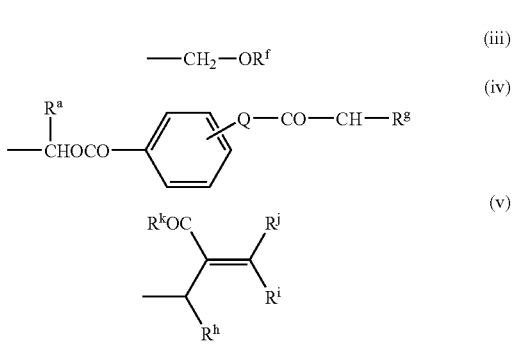

(iv)

(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-(($C_{1-6}$)alkoxycarbonyl)-2-$(C_{2-6})$alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

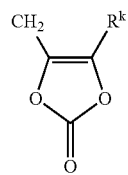

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group $CH(OH)$—$CH_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises reacting a compound of formula (IV) with a compound of formula (V):

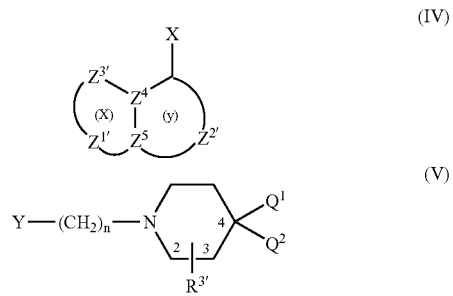

wherein n is as defined in formula (I); $Z^{1'}, Z^{2'}, Z^{3'}, R^{1'},$ and $R^{3'}$ are $Z^1, Z^2, Z^3, R^1,$ and $R^3$ as defined in formula (I) or groups convertible thereto; $Z^4$ and $Z^5$ are as defined in formula (I); $Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

(i) X is A'-COW, Y is H and n is 0;
(ii) X is $CR^6$=$CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is C(=O)$R^9$;
(vii) X is $CR^7$=$PR^z{}_3$ and Y is C(=O)$R^9$ and n=1;
(viii) X is C(=O)$R^7$ and Y is $CR^9$=$PR^z{}_3$ and n=1;
(ix) Y is COW and X is $NHR^{11'}$, NCO or NR11'COW and n=0 or 1 or when n=1 X is COW and Y is $NHR^{11'}$, NCO or NR11'COW;
(x) X is $NHR^{11'}$ and Y is C(=O)$R^8$ and n=1;
(xi) X is $NHR^{11'}$ and Y is $CR^8R^9W$ and n=1;
(xii) X is $NR^{11'}COCH_2W$ or $NR^{11'}SO_2CH_2W$ and Y is H and n=0;
(xiii) X is $CR^6R^7SO_2W$ and Y is H and n=0;
(xiv) X is W or OH and Y is $CH_2OH$ and n is 1;
(xv) X is $NHR^{11'}$ and Y is $SO_2W$ or X is $NR^{11'}SO_2W$ and Y is H, and n is 0;
(xvi) X is W and Y is $CONHR^{11'}$;
(xvii) X is —CH=$CH_2$ and Y is H and n=0;
(xviii) X is $CH_3$ and Y is H and n=0 together with formaldehyde in which W is a leaving group, e.g. halo, methanesulphonyloxy, trifluoromethanesulphonyloxy or imidazolyl; $R^x$ and $R^y$ are ($C_{1-6}$)alkyl; $R^z$ is aryl or ($C_{1-6}$)alkyl; A' and $NR^{11'}$ are A and $NR^{11}$ as defined in formula (I), or groups convertible thereto; and oxirane is:

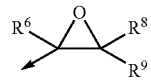

wherein $R^6$, $R^8$ and $R^9$ are as defined in formula (I);

and thereafter optionally or as necessary converting $Q^1$ and $Q^2$ to $NR^{2'}R^{4'}$; converting A', $Z^{1'}, Z^{2'}, Z^{3'}, R^{1'}, R^{2'}, R^{3'}, R^{4'}$ and $NR^{11'}$; to A, $Z^1, Z^2, Z^3, R^1, R^2, R^3, R^4$ and $NR^{11}$; converting A-B to other A-B, interconverting $R^1$, $R^2$, $R^3$ and/or $R^4$, and/or forming a pharmaceutically acceptable derivative thereof.

Process variant (i) initially produces compounds of formula (I) wherein A-B is A'-CO.

Process variant (ii) initially produces compounds of formula (I) wherein A-B is $CHR^6$—$CR^8R^9$.

Process variant (iii) initially produces compounds of formula (I) wherein A-B is $CR^6(OH)$—$CR^8R^9$.

Process variant (iv) initially produces compounds of formula (I) where A-B is NH—CO.

Process variant (v) initially produces compounds of formula (I) wherein A-B is CO—$CH_2$ or $CH_2$—CO.

Process variant (vi) initially produces compounds of formula (I) wherein A-B is $CR^6R^7$—$CR^9OH$.

Process variant (vii) and (viii) initially produce compounds of formula (I) wherein A-B is $CR^7$=$CR^9$.

Process variant (ix) initially produces compounds of formula (I) where A-B is CO—$NR^{11}$ or $NR^{11}$—CO.

Process variant (x) initially produces compounds of formula (I) wherein A-B is $NR^{11}$—$CHR^8$.

Process variant (xi) initially produces compounds of formula (I) wherein A-B is $NR^{11}$—$CR^8R^9$.

Process variant (xii) initially produces compounds of formula (I) where A-B is $NR^{11'}$—CO or $NR^{11'}$—$SO_2$ and n=1.

Process variant (xiii) initially produces compounds of formula (I) where A-B is $CR^6R^7$—$SO_2$.

Process variant (xiv) initially produces compounds of formula (I) wherein A-B is O—$CH_2$.

Process variant (xv) initially produces compounds where AB is $NR^{11}SO_2$.

Process variant (xvi) initially produces compounds of formula (I) where A-B is $NR^{11'}$—CO.

Process variants (xvii) and (xviii) initially produce compounds of formula (I) where A-B is —$CH_2$—$CH_2$—.

In process variants (i) and (ix) the reaction is a standard amide or urea formation reaction involving e.g.:

1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) *Suppl. B: The Chemistry of Acid Derivatives, Pt.* 1 (John Wiley and Sons, 1979), pp 442-8; Beckwith, A. L. J. in *The Chemistry of Functional Groups* (Ed. Patai, S.) *Suppl. B: The Chemistry of Amides* (Ed. Zabricky, J.) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or 2. The specific methods of:

a. in situ conversion of an acid into the amine component by a modified Curtius reaction procedure (Shioiri, T., Murata, M., Harnada, Y., *Chem. Pharm. Bull.* 1987, 35, 2698)

b. in situ conversion of the acid component into the acid chloride under neutral conditions (Villeneuve, G. B.; Chan, T. H., *Tetrahedron. Lett.* 1997, 38, 6489).

A' may be, for example, protected hydroxymethylene.

The process variant (ii) is a standard addition reaction using methods well known to those skilled in the art. The process is preferably carried out in a polar organic solvent e.g. acetonitrile in the presence of an organic base e.g. triethylamine.

In process variant (iii) the coupling may be effected in a suitable solvent such as acetonitrile or dimethylformamide at room temperature in the presence of one equivalent of lithium perchlorate as catalyst (general method of J. E. Chateauneuf et al, *J. Org. Chem.*, 56, 5939-5942, 1991) or more preferably with ytterbium triflate in dichloromethane. In some cases an elevated temperature such as 40-70° C. may be beneficial. Alternatively, the piperidine may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (iv) is a standard urea formation reaction from the reaction of an isocyanate with an amine and is conducted by methods well known to those skilled in the art (for example see March, J; *Advanced Organic Chemistry*, Edition 3 (John Wiley and Sons, 1985), p 802-3). The process is preferably carried out in a polar solvent such as N,N-dimethylformamide.

In process variant (v) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0-100° C. Analogous routes are described in DE330945, EP31753, EP53964 and H. Sargent, J. Am. Chem. Soc. 68, 2688-2692 (1946). Similar Claisen methodology is described in Soszko et. al., Pr. Kom. Mat. Przyr. Poznan. Tow. Przyj. Nauk., (1962), 10, 15.

In process variant (vi) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (vii) and (viii) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (x) where Y is CHO the reaction is a standard reductive alkylation using, e.g., sodium borohydride or sodium triacetoxyborohydride (Gribble, G. W. in *Encyclopedia of Reagents for Organic Synthesis* (Ed. Paquette, L. A.) (John Wiley and Sons, 1995), p 4649).

The process variant (xi) is a standard alkylation reaction well known to those skilled in the art, for example where an alcohol or amine is treated with an alkyl halide in the presence of a base (for example see March, J; *Advanced Organic Chemistry, Edition* 3 (John Wiley and Sons, 1985), p 364-366 and p 342-343). The process is preferably carried out in a polar solvent such as N,N-dimethylformamide In process variant (xii) the reaction is an alkylation, examples of which are described in J. Med. chem. (1979) 22(10) 1171-6. The compound of formula (IV) may be prepared from the corresponding compound where X is $NHR^{11'}$ by acylation with an appropriate derivative of the acid $WCH_2COOH$ such as the acid chloride or sulphonation with an appropriate derivative of the sulphonic acid $WCH_2SO_3H$ such as the sulphonyl chloride.

In process variant (xiii) the reaction is a standard sulphonamide formation reaction well known to those skilled in the art. This may be e.g. the reaction of a sulphonyl halide with an amine.

In process variant (xiv) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et al. J Chem Soc. (1995), 623). Alternatively the X=O and Y=$CH_2OH$ groups can be reacted directly by activation with 1,3-dicyclohexylcarbodiimide (DCC) (Chem. Berichte 1962, 95, 2997 or Angewante Chemie 1963 75, 377).

In process variant (xv) the reaction is conducted in the presence of an organic base such as triethylamine or pyridine such as described by Fuhrman et. al., J. Amer. Chem. Soc.; 67, 1245, 1945. The X=$NR^{11'}SO_2W$ or Y=$SO_2W$ intermediates can be formed from the requisite amine e.g. by reaction with $SO_2Cl_2$ analogously to the procedure described by the same authors Fuhrman et. al., J. Amer. Chem. Soc.; 67, 1245, 1945.

In process variant (xvi) the leaving group W is preferably chloro, bromo or iodo or trifluoromethylsulphonyloxy and the reaction is the palladium catalysed process known as the "Buchwald" reaction (J. Yin and S. L. Buchwald, Org. Lett., 2000, 2, 1101).

In process variant (xvii) the reaction is the addition of an amine to an olefin which is susceptible to nucleophilic attack.

In process variant (xviii) the reaction is a three component condensation reaction carried out under mildly acidic conditions.

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to $CH_2$ by treatment with a reducing agent such as hydrazine in ethylene glycol, at e.g. 130-160° C., in the presence of potassium hydroxide.

Reaction of a carbonyl group A or B with an organometallic reagent yields a group where $R^6$ or $R^8$ is OH and $R^7$ or $R^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group $CHR^7CR^9OH$ or $CR^7(OH)CHR^9$ may be dehydrated to give the group $CR^7$=$CR^9$ by treatment with an acid anhydride such as acetic anhydride.

Methods for conversion of $CR^7$=$CR^9$ by reduction to $CHR^7CHR^9$ are well known to those skilled in the art, for example using hydrogenation over palladium on carbon as catalyst. Methods for conversion of $CR^7$=$CR^9$ to give the A-B group $CR^7(OH)CHR^9$ or $CHR^7CR^9OH$ are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2R^4$ is $NR^{2'}R^{4'}$ or halogen. Halogen may be displaced by an amine $HNR^{2'}R^{4'}$ by a conventional alkylation.

When $Q^1Q^2$ together form a protected oxo group this may be an acetal such as ethylenedioxy which can subsequently be removed by acid treatment to give a compound of formula (VI):

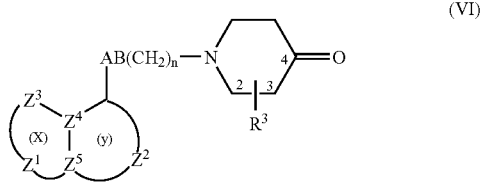

wherein the variables are as described for formula (I)

The ketone of formula (VI) is reacted with an amine $HNR^{2'}R^{4'}$ by conventional reductive alkylation as described above for process variant (x).

Examples of groups $Z^{1'}$, $Z^{2'}$ and $Z^{3'}$ convertible to $Z^1$, $Z^2$ and $Z^3$ include $CR^1$ or $CR^{1'}CR^{1a'}$ where $R^{1'}$ and $R^{1a'}$ are groups convertible to $R^1$ and $R^{1a}$. $Z^{1'}$, $Z^{2'}$ and $Z^{3'}$ are preferably $Z^1$, $Z^2$ and $Z^3$.

$R^{1a'}$, $R^{1'}$ and $R^{2'}$ are preferably $R^{1a}$, $R^1$ and $R^2$. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^{1'}$, $R^{1a'}$, $R^{2'}$, $R^3$ and $R^4$ and interconversions of $R^1$, $R^{1a}$, $R^2$, $R^3$ and $R^4$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1'}$ methoxy is convertible to $R^{1'}$ hydroxy by treatment with lithium and diphenylphosphine (general method described in Ireland et al, J. Amer. Chem. Soc., 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1]nonane, epoxidation and reduction or oxymercuration.

$R^3$ 1,2-dihydroxyalkyl can be prepared from $R^{3'}$ alkenyl using osmium tetroxide or other reagents well known to those skilled in the art (see Advanced Organic Chemistry, Ed. March, J., John Wiley and Sons, 1985, p 732-737 and refs. cited therein) or epoxidation followed by hydrolysis (see Advanced Organic Chemistry, Ed. March, J. John Wiley and Sons, 1985, p 332, 333 and refs. cited therein).

$R^3$ vinyl can be chain extended by standard homologation, e.g. by conversion to hydroxyethyl followed by oxidation to the aldehyde, which is then subjected to a Wittig reaction.

Opening an epoxide-containing $R^{3'}$ group with cyanide anion yields a CH(OH)—CH$_2$CN group.

Opening an epoxide-containing $R^{3'}$ group with azide anion yields an azide derivative which can be reduced to the amine. Conversion of the amine to a carbamate is followed by ring closure with base to give the 2-oxo-oxazolidinyl containing $R^3$ group.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, Ann. Chem., 1985, 1817; Rozenberg et al, Angew. Chem. Int. Ed. Engl., 1994, 33(1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols CH$_2$OH using chromic acid and sulphuric acid in water/methanol (E. R. H. Jones et al, J. Chem. Soc., 1946, 39). Other oxidising agents may be used for this transformation such as sodium periodate catalysed by ruthenium trichloride (G. F. Tutwiler et al, J. Med. Chem., 1987, 30(6), 1094), chromium trioxide-pyridine (G. Just et al, Synth. Commun., 1979, 9(7), 613), potassium permanganate (D. E. Reedich et al, J. Org. Chem., 1985, 50(19), 3535), and pyridinium chlorochromate (D. Askin et al, Tetrahedron Lett., 1988, 29(3), 277).

The carboxy group may alternatively be formed in a two stage process, with an initial oxidation of the alcohol to the corresponding aldehyde using for instance dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perruthenate (Ley et al, J. Chem. Soc. Chem Commun., 1987, 1625). The aldehyde may then be separately oxidised to the corresponding acid using oxidising agents such as silver (II) oxide (R. Grigg et al, J. Chem. Soc. Perkin 1, 1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, J. Am. Chem. Soc., 1982, 104, 2198).

An $R^3$ CO$_2$H group may also be prepared from oxidative cleavage of the corresponding diol, CH(OH)CH$_2$OH, using sodium periodate catalysed by ruthenium trichloride with an acetonitrile-carbontetrachloride-water solvent system (V. S. Martin et al, Tetrahedron Letters, 1988, 29(22), 2701).

Other routes to the synthesis of carboxy groups within $R^3$ are well known to those skilled in the art.

$R^3$ groups containing a cyano or carboxy group may also be prepared by conversion of an alcohol to a suitable leaving group such as the corresponding tosylate by reaction with para-toluenesulphonyl chloride (M. R. Bell, J. Med. Chem., 1970, 13, 389), or the iodide using triphenylphosphine, iodine, and imidazole (G. Lange, Synth. Commun., 1990, 20, 1473). The second stage is the displacement of the leaving group with cyanide anion (L. A. Paquette et al, J. Org. Chem., 1979, 44(25). 4603; P. A. Grieco et al, J. Org. Chem., 1988, 53(16), 3658. Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, J. Org. Chem., 1958, 23, 248) or enzymatically (T. Beard et al, Tetrahedron Asymmetry, 1993, 4 (6), 1085).

R³ cis or trans hydroxy may be introduced by the methods of van Deale et al., Drug Development Research 8:225-232 (1986) or Heterocycles 39(1), 163-170 (1994). For trans hydroxy, a suitable method converts N-protected tetrahydropyridine to the epoxide by treatment with metachloroperbenzoic acid, followed by opening of the epoxide with a suitable amine NR²'R⁴'. R³' hydroxy may then be converted to optionally substituted amino via preparation of the R³' amino derivative by standard transformations such as a Mitsunobu reaction (for example as reviewed in Misunobu, Synthesisi, (1981), 1), for example with succinimide in the presence of diethylazodicarboxylate and triphenylphosphine to give the phthalimidoethylpiperidine. Removal of the phthaloyl group, for example by treatment with methylhydrazine, affords the R³' amine. Optional substitution may then be introduced by standard methods for amine substitution well known to those skilled in the art.

R³ 4-CF₃ may be introduced by the following scheme I:

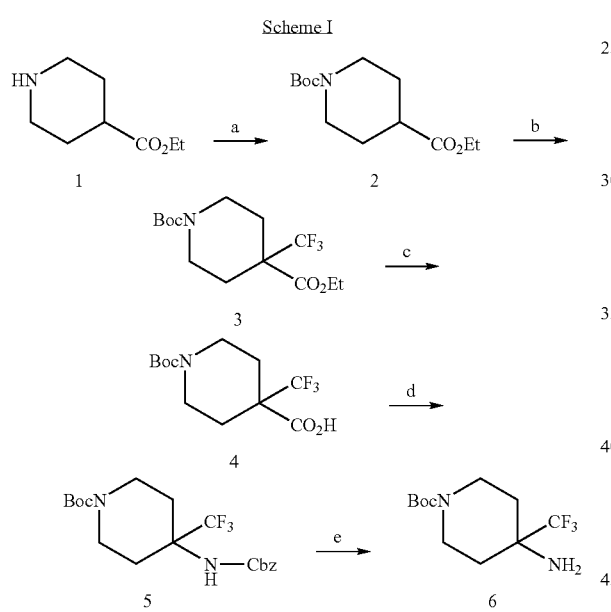

(a) (Boc)₂O, CH₂Cl₂; (b) LDA, then CF₃—X;
(c) NaOH, H₂O, EtOH; (d) DPPA, Et₃N, toluene, then BnOH; (e) H₂, Pd/C, EtOH.

Commercially-available ethyl isonipecotate (I-1) reacts with an appropriate acylating agent, preferably di-tert-butyl dicarbonate, to afford the protected derivative I-2. Typical solvents for this reaction include CH₂Cl₂, THF, or DMF. The protecting group for the amine must be compatible with subsequent chemistry, and must be readily removable when desired. Methods for the protection of amines are well-known to those of skill in the art, and are described in standard reference volumes, such as Greene "Protective Groups in Organic Synthesis" (published by Wiley-Interscience). Alkylation of I-2 can be accomplished by reaction with an appropriate base, typically LDA or LiN(TMS)₂, in an aprotic solvent, usually THF or DME, followed by trapping of the enolate with an appropriate electrophile, to afford I-3. Trifluoromethyl iodide (CF₃I) or S-(trifluoromethyl)dibenzothiophenium trifluoromethanesulfonate are typically preferred as electrophilic trifluoromethylating reagents. The ethyl ester of I-3 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-4. Curtius-type rearrangement of I-4 gives an intermediate isocyanate, which typically is not isolated, but rather is reacted in situ with an appropriate alcohol, such as benzyl alcohol, to give I-5. Diphenylphosphoryl azide in the presence of an amine base, generally triethylamine or diisopropylethylamine (Hunig's base), is the preferred reagent combination for effecting the Curtius-type rearrangement of I-4, but more classical conditions, such as formation of the acid chloride, reaction with azide anion, and warming of the acyl azide, can also be used. The benzyloxycarbonyl group in I-5 is removed by hydrogenolysis in the presence of a palladium catalyst, typically palladium on activated charcoal, in a suitable solvent, usually EtOH, MeOH, EtOAc, or mixtures thereof, to give amine I-6.

R³ 2-CF₃ may be introduced by the following scheme II:

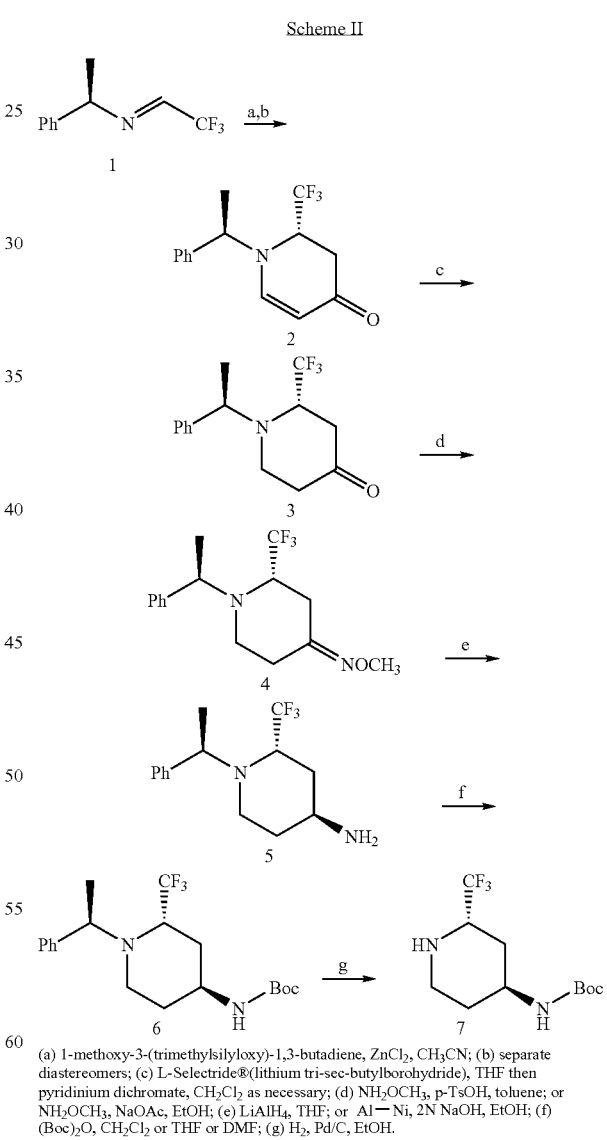

(a) 1-methoxy-3-(trimethylsilyloxy)-1,3-butadiene, ZnCl₂, CH₃CN; (b) separate diastereomers; (c) L-Selectride®(lithium tri-sec-butylborohydride), THF then pyridinium dichromate, CH₂Cl₂ as necessary; (d) NH₂OCH₃, p-TsOH, toluene; or NH₂OCH₃, NaOAc, EtOH; (e) LiAlH₄, THF; or Al—Ni, 2N NaOH, EtOH; (f) (Boc)₂O, CH₂Cl₂ or THF or DMF; (g) H₂, Pd/C, EtOH.

Imine II-1, prepared in standard fashion by acid-catalyzed reaction of trifluoroacetaldehyde ethyl hemiacetal and (R)-

(+)-α-methylbenzylamine, reacts with a silyloxydiene, for example 1-methoxy-3-(trimethylsilyloxy)-1,3-butadiene, in a Diels-Alder reaction to afford piperidone II-2. The reaction is conducted in a neutral solvent such as CH$_3$CN, THF, or CH$_2$Cl$_2$, and oftentimes is mediated by a Lewis acid such as ZnCl$_2$. Diastereomers are best separated at this point. The enone II-2 is reduced to the corresponding ketone II-3 by reaction with L-Selectride® in a suitable solvent, generally THF or DME, and the ketone is converted to an oxime derivative under standard conditions well-known to those of skill in the art. Reduction of the oxime derivative under standard conditions (LiAlH$_4$) gives a mixture of diastereomeric amines from which the amine II-5 can be isolated. The amine is protected with an appropriate protecting group, preferably a tert-butyl carbamate (see Scheme I), to afford II-6. The α-methylbenzyl group of II-6 is removed by hydrogenolysis in the presence of a palladium catalyst, typically palladium on activated charcoal, in a suitable solvent, usually EtOH, MeOH, EtOAc, or mixtures thereof, to give amine II-7.

R$^3$ 3-CF$_3$ may be introduced by the following scheme III:

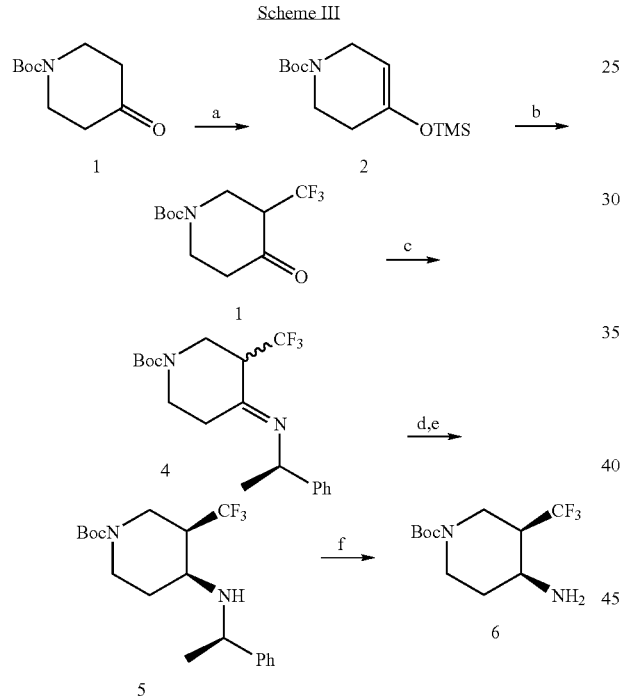

(a) TMSCl, Et$_3$N, DMF; (b) CF$_3$—X, DMF; (c) (R)-(+)-α-methylbenzylamine, p-TsOH, toluene; (d) NaBH$_4$, EtOH; (e) separate diastereomers; (f) H$_2$, Pd/C, EtOH.

The commercially-available ketone III-1 is converted to the corresponding silyl enroll ether III-2 by reaction with a silylating reagent, such a trimethylsilyl chloride or trimethylsilyl triflate, in the presence of an amine base, typically triethylamine, in a suitable solvent, such as diethyl ether, THF, DMF, or mixtures thereof. The silly enroll ether III-2 reacts with an electrophilic trifluoromethylating reagent, such as trifluoromethyl iodide (CF$_3$I) or more preferably S-(trifluoromethyl)dibenzothiophenium trifluoromethanesulfonate (see *Tet. Lett.* 1990, 31, 3579-3582)), in an appropriate solvent, such as THF, DMF, or mixtures thereof, to afford the α-trifluoromethyl ketone III-3. Ketone III-3 reacts with a chiral amine, for instance (R)-(+)-α-methylbenzylamine, under standard acidic catalysis, to afford the imine derivative III-4, which can be reduced to afford amine III-5.

This type of reduction is typically conducted using sodium borohydride, sodium cyanoborohydride or sodium (triacetoxy)borohydride, in an appropriate solvent, such as EtOH, MeOH, THF, CH$_2$Cl$_2$, ClCH$_2$CH$_2$Cl, or mixtures thereof. Diastereomers are best separated at this point. The α-methylbenzyl group of III-5 is removed by hydrogenolysis in the presence of a palladium catalyst, typically palladium on activated charcoal, in a suitable solvent, usually EtOH, MeOH, EtOAc, or mixtures thereof, to give amine III-6.

R$^3$ 2-oxo may be introduced by the following scheme IV:

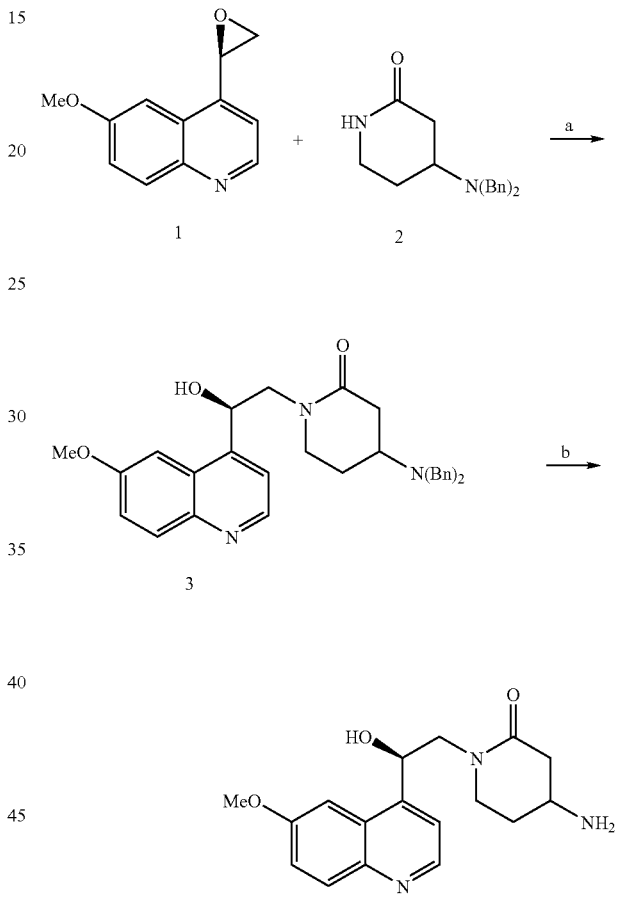

(a) NaH, THF, 0° C to RT; (b) 10% Pd/C, H$_2$, MeOH.

(R,S)-4-(Dibenzylamino)piperidin-2-one (IV-2, Homo-Freidinger Lactam, prepared from (R,S)-aspartic acid according to the procedure of Weber and Gmeiner, *Synlett,* 1998, 885-887) reacts with an appropriate epoxide, for instance 6-methoxy-4-(R)-oxiranylquinoline (VI-1) or 6-methoxy-4-(R)-oxiranyl-[1,5]naphthyridine, to afford the adduct IV-3. The reaction is mediated by a strong base, preferably sodium hydride, which is used to deprotonate IV-2, and is typically conducted in a polar, aprotic solvent, such as THF, DMF, or mixtures thereof. The benzyl groups in IV-3 are removed by hydrogenolysis in the presence of a palladium catalyst, typically palladium on activated charcoal, in a suitable solvent, usually EtOH, MeOH, EtOAc, or mixtures thereof, to give amine IV-4.

R³ 3-F may be introduced by the following scheme V:

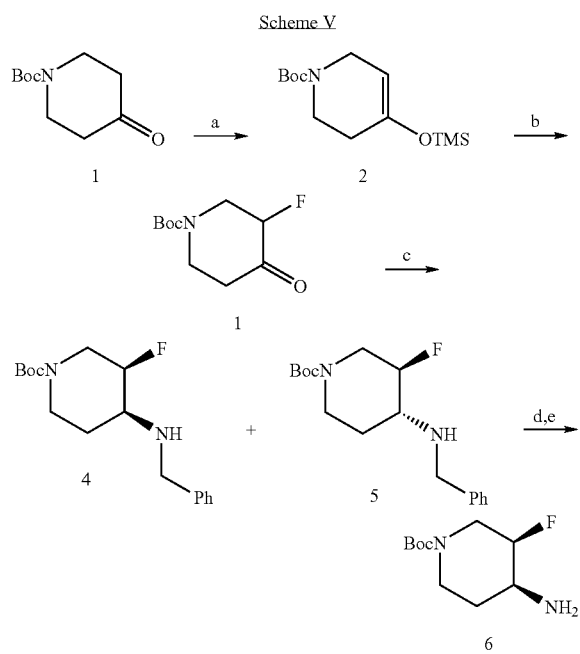

(a) TMSCl, Et₃N, DMF, 80° C., (b) Selectfluor™, CH₃CN; (c) benzylamine, 1,2-dichloroethane, Na(OAc)₃BH; (d) separate diastereomers; (e) 10% Pd/C, H₂, HCl, EtOH.

The trimethylsilyl enol ether (V-2), prepared from commercially-available N-(tert-butoxycarbonyl)piperidone (V-1) as described in Scheme III, reacts with an electrophilic fluorinating reagent, preferably Selectfluorin™ (1-chloromethyl-4-fluoro-1,4-diazabicyclo[2.2.2]octane bis(tetrafluoroborate), in a neutral solvent such as CH₃CN, to afford the α-fluoro ketone V-3. Reductive amination of V-3 with benzylamine according to the procedures described in Schemes I and III gives the expected 4-aminobenzyl-3-fluoro-N-(tert-butoxycarbonyl)piperidine derivatives V-4 and V-5 as a mixture of cis- and trans-isomers in an 8:1 ratio. These diastereomers are separable by chromatography on silica gel. The predominate cis-mixture of enantiomers is debenzylated by catalytic hydrogenation as described in Scheme II, to give the amino derivative V-6.

Other functional groups in R³ may be obtained by conventional conversions of hydroxy, carboxy or cyano groups.

Tetrazoles are conveniently prepared by reaction of sodium azide with the cyano group (e.g. F. Thomas et al, *Bioorg. Med. Chem. Lett.*, 1996, 6(6), 631; K. Kubo et al, *J. Med. Chem.*, 1993, 36, 2182) or by reaction of azidotri-n-butyl stannane with the cyano group followed by acidic hydrolysis (P. L. Ornstein, *J. Org. Chem.*, 1994, 59, 7682 and *J. Med. Chem.*, 1996, 39 (11), 2219).

The 3-hydroxy-3-cyclobutene-1,2-dion-4-yl group (e.g. R. M. Soll, *Bioorg. Med. Chem. Lett.*, 1993, 3(4), 757 and W. A. Kinney, *J. Med. Chem.*, 1992, 35(25), 4720) can be prepared by the following sequence: (1) a compound where R³ is (CH₂)ₙCHO (n=0, 1, 2) is treated with triethylamine, carbon tetrabromide/triphenylphosphine to give initially (CH₂)ₙCH=CHBr; (2) dehydrobromination of this intermediate to give the corresponding bromoethyne derivative (CH₂)ₙC≡CBr (for this 2 stage sequence see D. Grandjean et al, *Tetrahedron Lett.*, 1994, 35(21), 3529); (3) palladium-catalysed coupling of the bromoethyne with 4-(1-methylethoxy)-3-(tri-n-butylstannyl)cyclobut-3-ene-1,2-dione (Liebeskind et al, *J. Org. Chem.*, 1990, 55, 5359); (4) reduction of the ethyne moiety to —CH₂CH₂— under standard conditions of hydrogen and palladium on charcoal catalysis(see Howard et al, *Tetrahedron*, 1980, 36, 171); and finally (4) acidic hydrolysis of the methyl ethoxyester to generate the corresponding 3-hydroxy-3-cyclobutene-1,2-dione group (R. M. Soll, *Bioorg. Med. Chem. Lett.*, 1993, 3(4, 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, *J. Med Chem*, 1996, 39(11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, *J. Med. Chem.*, 1996, 39(11), 2232).

The hydroxamic acid groups are prepared from the corresponding acids by standard amide coupling reactions e.g. N. R. Patel et al, *Tetrahedron*, 1987, 43(22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is described by Y. Kohara et al, *Bioorg. Med. Chem. Lett.*, 1995, 5(17), 1903.

1,2,4-Triazol-5-yl groups may be prepared from the corresponding nitrile by reaction with an alcohol under acid conditions followed by reaction with hydrazine and then an R¹⁰-substituted activated carboxylic acid (see J. B. Polya in "Comprehensive Heterocyclic Chemistry" Edition 1, p 762, Ed A. R. Katritzky and C. W. Rees, Pergamon Press, Oxford, 1984 and J. J. Ares et al, *J. Heterocyclic Chem.*, 1991, 28(5), 1197).

Other substituents on R³ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

An NH₂ substituent on piperidine is converted to NR²R⁴ by conventional means such as amide or sulphonamide formation with an acyl derivative R⁵COW or R⁵SO₂W, for compounds where U is CO or SO₂ or, where U is CH₂, by alkylation with an alkyl halide R⁵CH₂-halide in the presence of base, acylation/reduction with an acyl derivative R⁵COW or reductive alkylation with an aldehyde R⁵CHO.

Where one of R³ and R⁶, R⁷, R⁸ or R⁹ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconversions may interfere, for example, A or B hydroxy groups in A or B and the piperidine substituent NH₂ will require protection e.g. as a carboxy- or silyl-ester group for hydroxy and as an acyl derivative for piperidine $NH_2$, during conversion of $R^{1'}$, $R^{2'}$, $R^{3'}$ or $R^{4'}$, or during the coupling of the compounds of formulae (IV) and (V).

Compounds of formulae (IV) and (V) are known compounds, (see for example Smith et al, *J. Amer. Chem. Soc.,* 1946, 68, 1301) or prepared analogously.

Compounds of formula (IV) where X is $CR^6R^7SO_2W$ may be prepared by a route analogous to that of Ahmed El Hadri et al, *J. Heterocyclic Chem.,* 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. *Chem. Pharm. Bull.* 35, 2698-2704 (1987)].

The 4-amino derivatives are commercially available or may be prepared by conventional procedures from a corresponding 4-chloro or 4-trifluoromethanesulphonate derivative by treatment with ammonia (O. G. Backeberg et. al., *J. Chem Soc.,* 381, 1942) or propylamine hydrochloride (R. Radinov et. al., *Synthesis,* 886, 1986).

4-Alkenyl compounds of formula (IV) may be prepared by conventional procedures from a corresponding 4-halogeno-derivative by e.g. a Heck synthesis as described in e.g. *Organic Reactions,* 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in *Heterocyclic Compounds,* 6, 324 (1957) Ed. R. C. Elderfield.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds,* 6, 324 (1957) Ed. R. C. Elderfield. These 4-carboxy derivatives maybe activated by conventional means, e.g. by conversion to an acyl halide or anhydride.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in he art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the equivalent intermediates can be attained by Stille coupling of the trifluoromethanesulphonates or the analogous chloro derivatives with (1-ethoxyvinyl)tributyl tin, (T. R. Kelly, J. Org. Chem., 1996, 61, 4623).) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85-95% [see C. Bohm et al, *Chem. Ber.* 125, 1169-1190, (1992)]. Recrystallisation of the chiral epoxide gives material in the mother liquor with enhanced optical purity (typically ee 95%).

The (R)-epoxide, when reacted with a piperidine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.,* 1987, 24, 853-857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.,* 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p 581-627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetophenone is diazotised with sodium nitrite and acid to produce the 4-hydroxycinnoline with conversion to chloro and amino derivatives as described for 1,5-naphthyridines.

R$^A$ groups where the ring (y) is 4-pyridyl are available by the sequence described below, starting from an aromatic or heterocyclic amine (1), with at least one free CH position adjacent to the amine. Reaction with Meldrum's acid and trimethyl orthformate in ethanol at reflux affords the corresponding 2,2-dimethyl-5-phenylaminomethylene-[1,3]dioxane-4,6-dione derivatives (2). These can be cyclised at elevated temperatures (180-220° C.) in inert solvents such as Dowtherm to give the corresponding 1H-quinolin-4-one (3) or heterocyclic analogues eg 1H-[1,6]naphthyridin-4-one. These processes are well-established and are described by Walz and Sundberg (J. Org. Chem., 2000, 65 (23), 8001) and by Todter and Lackner (Synthesis, 1997 (5) 576).

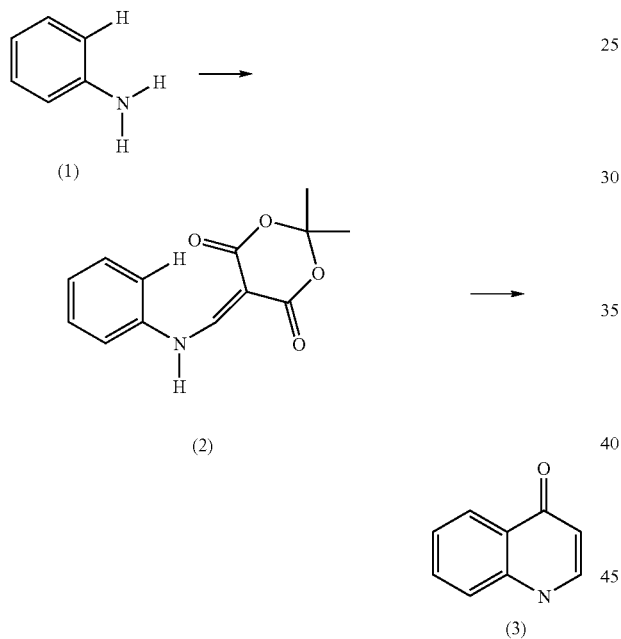

Activation of the quinolone species related to (3) into the corresponding 4-quinolyl bromides (4) can be accomplished with phosphorous oxybromide or more preferably phosphorous tribromide in N,N-dimethylformamide (see M. Schmittel et al, Synlett, 1997, (9), 1096 and K. Gould et al, J. Med., Chem., 1988, 31 (7), 1445). The corresponding chlorides (5) are available by using phosphoryl oxychloride (for instance C. W. Wright et al, J. Med., Chem., 2001, 44 (19), 3187).

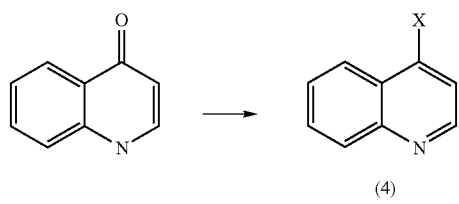

(4) X = Br
(5) X = Cl
(6) X = OTf

Alternatively, the quinolone species may be activated to the corresponding 1,1,1-trifluoro-methanesulfonic acid quinolin-4-yl esters (6) by the action of agents such as triflic anhydride or more preferably N-trifluoromethanesulphonimide (see for example M. Alvarez et al, Tet 2000, 56 (23) 3703; M. Alvarez et al, Eur. J. Org., Chem., 2000, (5), 849; J. Joule et al, Tet, 1998, 54 (17), 4405; J. K. Stille et al, J.A.C.S., 1988, 110 (12), 4051).

Activated species such as (4), (5), and (6) can then be subjected to a variety of metal-catalysed coupling reactions, such as amidation with primary carboxamides to give compounds such as (7) following the procedures of S. L. Buchwald et al (J.A.C.S., 2001, 123, 4051 and 7727; Org. Lett., 1999, 1, 35) or Sonogashira coupling with acetylenes to give compounds such as (8) (see A. Droz et al, Helv. Chim. Acta., 2001, 84 (8), 2243; M. Belly et al, Synlett, 2001 (2), 222; M. Pirrung et al, J.A.C.S., 2001, 123 (16), 3638).

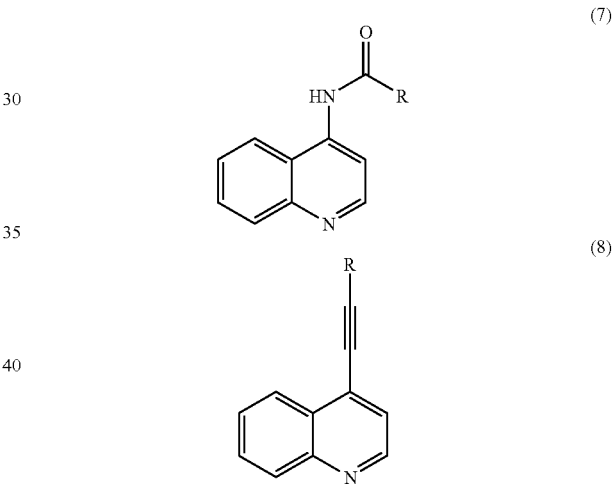

R$^A$ thieno[3,2-b]pyridin-7-yl, 2,3-dihydro-[1,4]dioxino[2,3-b]pyridin-8-yl, quinolin-8-yl and isoquinolin-5-yl derivatives are commercially available or prepared by conventional methods from commercially available or literature derivatives, for example 4H-thieno[3,2-b]pyridin-4-one, 2,3-dihydro-[1,4]dioxino[2,3-b]pyridine (prepared by the method of H. Neunhoffer et al, Chem., Ber., 1990, 123), 2-methoxyquinolin-8-ylamine (prepared by the method of K. Mislow et al J.A.C.S. 68, 1353 (1946)), 2,8-quinolinediol or trifluoromethane sulphonic acid-isoquinolin-5-yl ester (prepared as in D. Ortwine et al, J. Med. Chem., 1992, 35 (8), 1345).

R$^A$ quinoxalin-5-yl derivatives may be obtained from 2- or 3-methylquinoxalin-5-ol prepared as described by Y. Abe et al, J. Med. Chem., 1998, 41 (21), 4062 or from suitable substituted derivatives prepared by analogous methods. R$^A$ 3-methoxyquinoxaline-5-yl derivatives may be obtained from 3-oxoquinoxalin-5-yl prepared by the general methods of F. J. Wolf et al., J.A.C.S. 1949, 71, 6, using a suitable methylating agent such as trimethylsilyl(diazomethane). The corresponding 1,2,3,4-tetrahydro-quinoxalin-5-yl may be prepared by reduction with a suitable reducing agent such as sodium cyanoborohydride in the presence of an acid such as acetic acid.

The isoquinolin-8-yl system can be prepared from the appropriately substituted benzylamine by cyclocondensation with diethoxy-acetaldehyde (see, for example, K. Kido and Y. Watanabe, Chemical & Pharmaceutical Bulletin, 35(12), 4964-6; 1987). Alternatively 8-bromo-isoquinoline (prepared by the method of F. T. Tyson, J.A.C.S., 1939, 61, N. Briet et al., Tetrahedron (2002), 58(29), 5761-5766 or W. D. Brown, et al., Synthesis (2002), (1), 83-86. 183 can be subjected to N-oxidation and rearrangement to give 8-bromo-2H-isoquinolin-1-one. This can be N-methylated to give 8-bromo-2-methyl-2H-isoquinolin-1-one, an appropriate intermediate for the 2-methyl-1-oxo-1,2-dihydroisoquinolin-8-yl system.

The 1-methoxy-isoquinolin-8-yl system can also be obtained from the 8-bromoisoquinoline-N-oxide above by rearrangement with methyl chloroformate to give 8-bromo-1-methoxy-isoquinoline, an appropriate intermediate for the 1-methoxy-isoquinolin-8-yl system.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.,* 1984, 25, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis,* (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

$R^5CH_2$-halides, acyl derivative $R^5COW$ and $R^5SO_2W$ or aldehydes $R^5CHO$ are commercially available or are prepared conventionally. The aldehydes may be prepared by partial reduction of the $R^5$-ester with lithium aluminium hydride or di-isobutylaluminium hydride or more preferably by reduction to the alcohol, with lithium aluminium hydride or sodium borohydride or lithium triethylborohydride (see *Reductions by the Alumino- and Borohydrides in Organic Synthesis,* 2nd ed., Wiley, N.Y., 1997; *JOC,* 3197, 1984; Org. Synth. Coll., 102, 1990; 136, 1998; *JOC,* 4260, 1990; *TL,* 995, 1988; *JOC,* 1721, 1999; *Liebigs Ann./Recl.,* 2385, 1997; *JOC,* 5486, 1987), followed by oxidation to the aldehyde with manganese (II) dioxide, or by a 'Swern' procedure (oxalyl chloride/DMSO), or by using potassium dichromate (PDC). The aldehydes may also be prepared from carboxylic acids in two stages by conversion to a mixed carbonate for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivative $R^5COW$ may be prepared by activation of the $R^5$-ester. $R^5CH_2$-halides such as bromides may be prepared from the alcohol $R^5CH_2OH$ by reaction with phosphorus tribromide in DCM/triethylamine.

Alternatively the aldehyde $R^5CHO$ and sulphonic acid derivative $R^5SO_2W$ may be generated by treatment of the $R^5H$ heterocycle with suitable reagents. For example benzoxazinones, or more preferably their N-methylated derivatives can be formylated with hexamine in either trifluoroacetic acid or methanesulfonic acid, in a modified Duff procedure [O. I. Petrov et al. *Collect. Czech. Chem. Commun.* 62, 494-497 (1997)]. 4-Methyl-4H-benzo[1,4]oxazin-3-one may also be formylated using dichloromethyl methyl ether and aluminium chloride giving exclusively the 6-formyl derivative. Reaction of a $R^5H$ heterocycle with chlorosulphonic acid gives the sulphonic acid derivative (by methods analogous to Techer et. al., C. R. Hebd. *Seances Acad. Sci. Ser. C;* 270, 1601, 1970).

The aldehyde $R^5CHO$ may be generated by conversion of an $R^5$halogen or $R^5$trifluoromethane sulphonyloxy derivative into an olefin with subsequent oxidative cleavage by standard methods. For example, reaction of a bromo derivative under palladium catalysis with trans-2-phenylboronic acid under palladium catalysis affords a styrene derivative which upon ozonolysis affords the required $R^5CHO$ (Stephenson, G. R., Adv. Asymmetric Synth. (1996), 275-298. Publisher: Chapman & Hall, London).

$R^5H$ heterocycles are commercially available or may be prepared by conventional methods. For example where a benzoxazinone is required, a nitrophenol may be alkylated with for example ethyl bromoacetate and the resulting nitro ester reduced with Fe in acetic acid (alternatively Zn/AcOH/HCl or $H_2$/Pd/C or $H_2$/Raney Ni). The resulting amine may undergo spontaneous cyclisation to the required benzoxazinone, or cyclisation may be induced by heating in acetic acid. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chim. Ther.* 24, 55-60 (1989)]. The same general routes can be applied to prepare benzothiazinones [See for example F. Eiden and F. Meinel, Arch. Pharm. 312, 302-312 (1979), H. Fenner and R Grauert *Liebigs. Ann. Chem.* 193-313 (1978)]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde may be accessed from 5-fluoro-2-picoline (E. J. Blanz, F. A. French, J. R. DoAmaral and D. A. French, J. Med. Chem. 1970, 13, 1124-1130) by constructing the thiazinone ring onto the pyridyl ring then functionalising the methyl substituent. The dioxin analogue of this aza substitution pattern, 2,3-dihydro-[1,4]dioxino[2,3-c]pyridine-7-carbaldehyde is accessible from Kojic acid by aminolysis from pyrone to pyridone then annelating the dioxin ring. Other aza substitution patterns with pyridothiazin-3-one, pyridooxazin-3-one, and pyridodioxin ring systems are also accessible. Ortho-aminothiophenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene or triphosgene. Reaction of benzoxazolones with diphosphorus pentasulfide affords the corresponding 2-thione. Thiazines and oxazines can be prepared by reduction of the corresponding thiazinone or oxazinone with a reducing agent such as lithium aluminium hydride.

The amines $R^2R^4NH$ are available commercially or prepared conventionally. For example amines $R^5CH_2NH_2$ may be prepared from a bromomethyl derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Conversions of $R^{1a'}$, $R^{1'}$, $R^{2'}$, $R^{3'}$ and $R^{4'}$ maybe carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial "split and mix" approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

Abbreviations in the Examples:

RT=room temperature

ES=Electrospray mass spec.

LCMS=Liquid chromatography mass spec.
APCI+=Atmospheric pressure chemical ionisation mass spec

EXAMPLES

Example 1

4-2-{4-[(3-Oxo-3,4-dihydro-2H-pyrido[3,2-b][1,4]
oxazin-6-ylmethyl)-amino]-piperidin-1-yl}-ethyl)-
quinoline-6-carbonitrile dihydrochloride

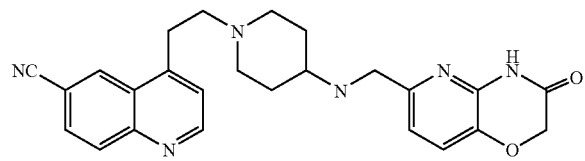

(a) 4-[(2,2-Dimethyl-4,6-dioxo-[1,3]dioxan-5-ylidenemethyl)-amino]-benzonitrile

A mixture of 4-amino-benzonitrile (12.5 g, 0.106 mol), 2,2-dimethyl-[1,3]dioxane-4,6-dione (18.3 g, 0.127 mol) and trimethylorthoformate (16 ml) in ethanol (100 ml) was refluxed for 3 hours. After cooling the solid was filtered off, washed with ethanol and air dried. The product was obtained as an off-white solid (27.9 g, 97%).

MS (+ve ion electrospray) m/z 273 (MH+).

(b) 4-Oxo-1,4-dihydro-quinoline-6-carbonitrile

Intermediate (a) (27.5 g, 0.101 mol) was slowly added over five minutes to refluxing Dowtherm A (200 ml). After an additional five minutes at reflux, the mixture was allow to cool to room temperature then ether (200 ml) was added. The product was filtered off, thoroughly washed with ether then air dried to afford the product as a gold coloured solid (16.2 g, 94%).

MS (+ve ion electrospray) m/z 171 (MH+).

(c) 4-Bromo-quinoline-6-carbonitrile

To a solution of (b) (12 g, 70.5 mmol) in DMF (75 ml) was added dropwise phosphorous tribromide (8 ml, 84.6 mmol) over five minutes (slightly exothermic). The reaction was allowed to cool to room temperature and was then diluted with ice water (100 ml) and stirred 1 hour then diluted with additional water (300 ml). The product was filtered off, washed with water and air dried to provide 14.3 g of product (87%).

MS (+ve ion electrospray) m/z 233 (MH+).

(d) 4-Vinyl-quinoline-6-carbonitrile

To a solution of (c) (1 g, 4.3 mmol) and vinyltributyltin (1.5 mL, 5.17 mmol) in degassed toluene (20 ml) was added tetrakis(triphenylphosphine) palladium (0) (245 mg, 5 mol %) and the mixture was refluxed under argon for 2 hours. Evaporation and flash silica chromatography eluting with chloroform afforded the product as a pale yellow solid (500 mg, 64%).

MS (+ve ion electrospray) m/z 181 (MH+).

(e) {1-[2-(6-Cyano-quinolin-4-yl)-ethyl]-piperidin-4-yl}-carbamic acid tert-butyl ester A mixture of (d) (150 mg, 0.8 mmol), piperidin-4-yl-carbamic acid tert-butyl ester (166 mg, 0.8 mmol) and chloroform (0.5 ml) were heated at 50° C. in a loosely capped vial for 6 hours. The product was purified by flash silica chromatography eluting with a 0-2% methanol in chloroform gradient affording the product as a foam (304 mg, 96%).

MS (+ve ion electrospray) m/z 381 (MH+).

(f) 2-Bromo-5-hydroxy-6-nitropyridine

3-Hydroxy-2-nitropyridine (20 g, 0.143 mole) was dissolved in methanol (400 ml) and a solution of 25% sodium methoxide in methanol (33 ml, 0.13 mol) was added at room temperature. The mixture was stirred for 30 minutes, then cooled to 0° C., and bromine (7.2 ml, 0.14 mol) was added slowly. The reaction was then stirred at 0° C. for 30 minutes, then was quenched with glacial AcOH (2.5 ml). The solvent was removed in vacuo to afford material (30 g, 96%), which was used without further purification.

MS (+ve ion electrospray) m/z 219 (MH+).

(g) Ethyl (6-bromo-2-nitro-pyridin-3-yloxy)acetate

The hydroxypyridine (f) (30 g, 0.14 mol) was suspended in acetone (200 ml), and potassium carbonate (39 g, 0.28 mol) was added, followed by ethyl bromoacetate (15.7 ml, 0.14 mmol). The reaction was heated at reflux for 10 hours, then was cooled to room temperature and diluted with Et$_2$O. The precipitate was removed by suction filtration, and the filtrate was concentrated in vacuo to afford material (38 g, 89%), which was used without further purification.

MS (+ve ion electrospray) m/z 305 (MH+).

(h) 6-Bromo-4H-pyrido[3,2-b][1,4]oxazin-3-one

The nitropyridine (g) (38 g, 0.125 mol) was dissolved in glacial AcOH (150 ml), and iron powder (20 g, 0.36 mole) was added. The mixture was mechanically stirred and heated at 90° C. for 5 hours, then was cooled to room temperature and diluted with EtOAc (300 ml). The mixture was filtered through a pad of silica gel and the filtrate was concentrated in vacuo and the residue recrystallized from MeOH (15 g, 52%).

MS (+ve ion electrospray) m/z 229 (MH+).

(i) 6-((E)-Styryl)-4H-pyrido[3,2-b][1,4]oxazin-3-one

The bromopyridine (h) (6.0 g, 26.3 mmol) and trans-2-phenylvinylboronic acid (3.9 g, 26.3 mmol) were dissolved in 1,4-dioxane (150 ml) and the solution was degassed with argon. (Ph$_3$P)$_4$Pd (230 mg, 0.2 mmol) was added, followed by a solution of potassium carbonate (6.9 g, 50 mmol) in water (20 ml). The reaction was heated at reflux under argon overnight, then was cooled to room temperature and diluted with EtOAc (200 ml). The solution was washed sequentially with water and brine, dried (Na$_2$SO$_4$), and concentrated in vacuo. The solid residue was purified by flash chromatography on silica gel (5-10% EtOAc/CHCl$_3$) to afford a solid (2.5 g, 38%).

MS (+ve ion electrospray) m/z 253 (MH+).

(j) 3-Oxo-3,4-dihydro-2H-pyrido[3,2-b][1,4]oxazine-6-carboxaldehyde

The pyridine (i) (1.2 g, 4.8 mmol) was dissolved in dichloromethane (200 ml) and the solution was cooled to −78° C. Ozone was bubbled through the solution with stirring until a pale blue color appeared, then the excess ozone was removed by bubbling oxygen through the solution for 15 min. Dimethylsulfide (1.76 ml, 24 mmol) was added to the solution, and the reaction was stirred at −78° C. for 3 hours, then at room temperature overnight. The solvent was removed in vacuo, and the residue was triturated with Et$_2$O (50 ml). The collected solid was washed with additional Et$_2$O and dried to afford a solid (700 mg, 82%).

MS (+ve ion electrospray) m/z 179 (MH+).

(k) Title Compound:

A solution of (e) (119 mg, 0.31 mmol) in dichloromethane (2 ml) was treated with trifluoroacetic acid (2 ml) dropwise and then stirred at room temperature for 1 hour. Evaporation to dryness gave the crude trifluoroacetate salt of the amine which was redissolved in dichloromethane (3 ml) and methanol (1 ml). Aldehyde (j) (55 mg, 0.31 mmol) and triethylamine (0.17 ml) were added and the mixture was stirred at room temperature overnight. Sodium borohydride (38 mg, 1 mmol) was added and the reaction was allowed to stir for 1 hour. Dilution with chloroform, washing with saturated aqueous sodium bicarbonate, drying and evaporation gave an oil. Chromatography on silica gel eluting with 2-10% methanol in chloroform afforded the free base of the title compound as an oil. Redissolving in ethylacetate-methanol and treatment with 2 equivalents of HCl precipitated the dihydrochloride salt of the product which was filtered, washed with ether and dried (45 mg, 26%)

$^1$H NMR (MeOH-d4, 400 MHz): 8.92 (d, 1H), 8.48 (d, 1H), 8.20 (d, 1H), 7.84 (dd, 1H), 7.40 (d, 1H), 7.20 (d, 1H), 6.94 (d, 1H), 4.65 (s, 2H), 3.85 (s, 2H), 3.28 (m, 2H), 3.02 (m, 2H), 2.72 (m, 2H), 2.56 (m, 1H), 2.15 (m, 2H), 1.96 (m, 2H), 1.54 (m, 2H). MS (+ve ion electrospray) m/z 443 (MH+).

Example 2

6-({(3R,4S)-3-Fluoro-1-[(R)-2-hydroxy-2-(2-methoxy-quinolin-8-yl)-ethyl]-piperidin-4-ylamino}-methyl)4H-pyrido[3,2-b][1,4]thiazin-3-one dihydrochloride and 6-({(3S,4R)-3-Fluoro-1-[(R)-2-hydroxy-2-(2-methoxy-quinolin-8-yl)-ethyl]-piperidin-4-ylamino}-methyl)4H-pyrido[3,2-b][1,4]thiazin-3-one dihydrochloride

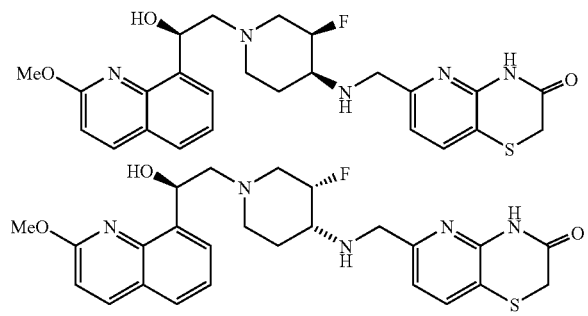

(a) 8-Benzyoxyquinolin-2-ol

To a stirred solution of 2,8-quinolinediol (30.84 mmol, 4.97 g; Fluka) and DBU (40.2 mmol, 6 mL) in isopropyl alcohol (60 mL) was added benzyl bromide (30.84 mmol, 3.7 mL). The solution was heated at reflux overnight. The reaction mixture was allowed to cool and then concentrated in vacuo. The resulting residue was diluted with CH$_2$Cl$_2$ and washed with 0.5 N NaOH, 10% HCl and water and dried over Na$_2$SO$_4$. Concentration provided 6 g (77%) of the tan solid, which was used without further purification. LC/MS: (ES) m/z 252 (M+H)$^+$.

(b) 8-Benzyloxy-2-methoxyquinoline

8-Benzyloxyquinolin-2-ol (a) (6 g, 23.9 mmol) was added to POCl$_3$ (45 mL) and heated with stirring at 80° C. for 10 h. The reaction was allowed to cool to room temperature and the excess POCl$_3$ was decomposed by slowly pouring the mixture into water at 30° C. The product was then extracted into toluene and the combined organic layers were washed with saturated aq. NaHCO$_3$ and dried over MgSO$_4$. Concentration provided 6.9 g of a colorless oil, crude 2-chloro-8-benzyloxyquinoline, which was directly used in the next reaction step. LC/MS: (ES) m/z 270 (M+H)$^+$.

The crude 2-chloro-8-benzyloxyquinoline from above was dissolved in toluene (10 mL) and added to a stirred 25 wt % solution of NaOMe in MeOH (50 mL). The reaction solution was heated with stirring overnight at 70° C. After cooling to room temperature, the reaction solution was poured onto ice and extracted with toluene. The combined organic extracts were dried (MgSO$_4$) and concentrated in vacuo to give a colorless oil (6.14 g, 92%). The product was used without further purification.

LC/MS: (ES) m/z 266 (M+H)$^+$.

(c) 1,1,1-Trifluoromethanesulfonic acid 2-methoxyquinolin-8-yl ester

8-Benzyloxy-2-methoxyquinoline (b) (6.14 g, 23 mmol) was dissolved in EtOH (50 mL) and treated with 10% Pd/C (600 mg). The reaction mixture was hydrogenated under an H$_2$ atmosphere (20 psi) in a Parr shaker apparatus for 3.5 h. The reaction was filtered and concentrated to give 3.8 g (96%) of a colorless oil.

LC/MS: (ES) m/z 176 (M+H)$^+$.

The product from above (3.8 g, 22 mmol) was dissolved in DMF (40 mL) and treated with triethylamine (3.6 mL, 25.8 mmol) and N-phenyltrifluoromethanesulfonimide (8.54 g, 23.9 mmol). The reaction mixture was heated with stirring at 40° C. for 8 h. Upon cooling to room temperature, aq. K$_2$CO$_3$ solution was added and the product was extracted into CH$_2$Cl$_2$. The combined organic extracts were washed with water (5×75 mL), dried (Na$_2$SO$_4$) and concentrated to give 6.8 g (100%) of triflate as a light tan crystalline solid, which was used directly in the next reaction without additional purification. LC/MS: (ES) m/z 308 (M+H)$^+$.

(d) 2-Bromo-1-(2-methoxy-quinolin-8-yl)-ethanone

The triflate (2c) in DMF, triethylamine, butyl vinyl ether, palladium (II) acetate and 1,3-bis(diphenylphosphino)propane is heated at 60° C. for 3 hours then evaporated and chromatographed on silica gel (dichloromethane). The product is dissolved in TBF and water and treated with N-bromosuccinimide for 1 hour, then evaporated and chromatographed on silica gel to give the ketone.

(e) (R)-2-Bromo-1-(2-methoxy-quinolin-8-yl)-ethanol

The ketone (2d) in toluene is treated with (+)-B-chlorodiisopinocamphenylborane ((+)-DIP-chloride) and stirred overnight, then diethanolamine is added and the mixture is stirred for 3 hours, filtered and then evaporated. Chromatography on silica gel gives the product.

(f) 2-Methoxy-8-(R)-oxiranyl-quinoline

The alcohol (e) in methanol is stirred with potassium carbonate for 1 hour, then is evaporated and chromatographed on silica gel to give the product.

(g) (3R, 4S) and (3S, 4R)-4-Amino-1-tert-butoxycarbonyl-3-fluoropiperidine

To a solution of the enantiomeric mixture of cis-4-benzylamino-1-tert-butoxycarbonyl-3-fluoropiperidine (prepared according to the procedures of *J. Med. Chem.* 1999, 42, 2087-2104, 1.0 g, 3.2 mmole) in EtOH (40 mL) was added 3 N HCl (2.5 L) and 10% Pd/C (50 mg). The reaction was shaken under H$_2$ (40 psi) on a Parr apparatus for 14 h, then was filtered through Celite®. The filtrate was concentrated under reduced pressure, and the residue was purified by flash chromatography on silica gel (10% MeOH/CHCl$_3$) to afford the title compound (370 mg, 53%) as a white solid.

MS (ES) m/e 219 (M +H)$^+$.

(h) (3R,4S) and (3S,4R)-4-Benzyloxycarbonylamino-3-fluoro-piperidine-1-carboxylic acid tert-butyl ester The amine (2 g) (5.49 g) in dichloromethane (150 ml) containing triethylamine (3.5 ml) was treated with benzyl chloroformate (4.0 ml) and stirred at room temperature for 5 hr. It was evaporated and chromatographed on silica gel to afford the product (4.27 g).

(i) ((3R,4S) and (3S,4R)-3-Fluoro-piperidin-4-yl)-carbamic acid benzyl ester

The carbamate (2 h) (4.27 g) was treated with trifluoroacetic acid (8 ml) in dichloromethane (40 ml) at room temperature for 3 hr then evaporated to dryness. The residue was basified with sodium carbonate and extracted with 10% methanol-dichloromethane. The solution was dried (sodium sulfate) and evaporated to give the product as a white solid (2.92 g).

(j) {(3R,4S) and (3S,4R)-3-Fluoro-1-[(R)-2-hydroxy-2-(2-methoxy-quinolin-8-yl)-ethyl]-piperidin-4-yl}-carbamic acid benzyl ester A 1:1 mixture of oxirane (2f) and piperidine (2i) is heated at 85° C. for 3 hr and the product chromatographed on silica gel.

(k) (R)-2-((3R,4S) and (3S,4R)-4-Amino-3-fluoro-piperidin-1-yl)-1-(2-methoxy-quinolin-8-yl)-ethanol The carbamate (2j) is hydrogenated in methanol at room temperature over 10% palladium charcoal, filtered and evaporated to afford the product.

(l) Methyl 3-oxo-3,4-dihydro-2H-pyrido[3,2-b][1,4]thiazine-6-carboxylate

A solution of ethyl 2-mercaptoacetate (1.473 ml) in DMF (48 ml) was ice-cooled and treated with sodium hydride (540 mg of a 60% dispersion in oil). After 1 hour methyl 6-amino-5-bromopyridine-2-carboxylate (3 g) (T. R. Kelly and F. Lang, *J. Org. Chem.* 61, 1996, 4623-4633) was added and the mixture stirred for 16 hours at room temperature. The solution was diluted with EtOAc (1 litre), washed with water (3×300 ml), dried and evaporated to about 10 ml. The white solid was filtered off and washed with a little EtOAc to give the ester (0.95 g).

MS (APCI⁻) m/z 223 ([M−H]⁻, 100%)

(m) 3-Oxo-3,4-dihydro-2H-pyrido[3,2-b][1,4]thiazine-6-carboxylic acid

A solution of ester (2l) (788 mg) in dioxan (120 ml)/water (30 ml) was treated dropwise over 2 hours with 0.5 M NaOH solution (8 ml) and stirred overnight. After evaporation to approx. 3 ml, water (5 ml) was added and 2N HCl to pH4. The precipitated solid was filtered off, washed with a small volume of water and dried under vacuum to give a solid (636 mg).

MS (APCI⁻) m/z 209 ([M−H]⁻, 5%), 165([M−COOH]⁻, 100%)

(n) 6-Hydroxymethyl-3-oxo-3,4-dihydro-2H-pyrido[3,2-b][1,4]thiazine

A solution of the carboxylic acid (2m) (500 mg) in THF (24 ml) with triethylamine (0.396 ml) was cooled to −10° C. and isobutyl chloroformate (0.339 ml) added. After 20 minutes the suspension was filtered through kieselguhr into an ice-cooled solution of sodium borohydride (272 mg) in water (8 ml), the mixture stirred 30 minutes and the pH reduced to 7 with dilute HCl. The solvent was evaporated and the residue triturated under water. The product was filtered and dried under vacuum to give a white solid (346 mg).

MS (APCI⁻) m/z 195 ([M−H]⁻, 50%), 165(100%)

(o) 3-Oxo-3,4-dihydro-2H-pyrido[3,2-b][1,4]thiazine-6-carboxaldehyde

A solution of the alcohol (2n) (330 mg) in dichloromethane (30 ml)/THF (30 ml) was treated with manganese dioxide (730 mg) and stirred at room temperature. Further manganese dioxide was added after 1 hour (730 mg) and 16 hours (300 mg). After a total of 20 hours the mixture was filtered through kieselguhr and the filtrate evaporated. The product was triturated with EtOAc/hexane (1:1) and collected to give a solid (180 mg).

MS (APCI⁻) m/z 195 ([M−H]⁻, 95%), 165 (100%)

(p) Title Compound

A mixture of the carboxaldehyde (2o) and amine (2k) (100 mg) in DMF/methanol/acetic acid with 3A molecular sieves is heated at 85° C. for 2 hours, cooled and is treated with an excess of sodium cyanoborohydride. After stirring overnight, the mixture is diluted with chloroform (20 ml) and washed with aqueous Na₂CO₃. The organic fraction is dried and evaporated. Chromatography of the residue on silica gel gives the free base of the title compound. Treatment with 4M HCl in dioxan, evaporation and trituration with ether affords the title compound Example 3

6-({(3R,4R)-3-Hydroxy-1-[(R)-2-hydroxy-2-(2-methoxy-quinolin-8-yl)-ethyl]-piperidin-4-ylamino}-methyl)4H-pyrido[3,2-b][1,4]thiazin-3-one dihydrochloride and 6-({(3S,4S)-3-Hydroxy-1-[(R)-2-hydroxy-2-(2-methoxy-quinolin-8-yl)-ethyl]-piperidin-4-ylamino}-methyl)-4H-pyrido[3,2-b][1,4]thiazin-3-one dihydrochloride

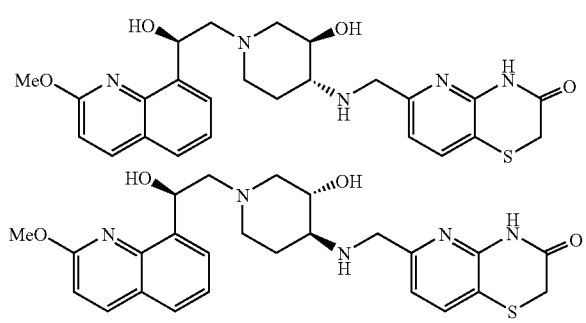

(a) tert-Butyl 3,6-dihydro-2H-pyridine-1-carboxylate 1,2,3,6-tetrahydropyridine (15.0 g, 180 mmole) was added to a 10% aqueous solution of Na₂CO₃ (50 ml) and the solution was cooled to 0° C. Di-tert-butyl dicarbonate (39.8 g, 182 mmole) was added in portions over 15 min with vigorous stirring. The solution was stirred at 0° C. for 1 hr and then warmed to room temperature and stirred for an additional 18 hr. The reaction solution was partitioned between Et₂O and saturated NaCl solution. The ether layer was dried over Na₂SO₄ and concentrated in vacuo to give an oil (31.80 g, 96%), which needed no further purification.

MS (ES) m/z 184 (M+H)⁺.

(b) tert-Butyl 7-oxa-3-aza-bicyclo[4.1.0]heptane-3-carboxylate

A solution of (3a) (15.0 g, 81.9 mmole) in CH₂Cl₂ (150 mL) was treated with a solution of meta-chloroperbenzoic acid (18.36 g, 106.4 mmole) in CH₂Cl₂ (300 mL) which was added over 30 minutes at 0° C. The solution was allowed to warm to room temperature and stirred for 18 hr. The reaction solution was washed with 5% aqueous $K_2CO_3$ and saturated NaCl solution, then dried over $Na_2SO_4$ and concentrated in vacuo to yield an off-white solid. This was flash chromatographed on silica gel (20% EtOAc/hexanes) to yield a white solid (12.80 g, 78%).

MS (ES) m/z 200 (M+H)$^+$.

(c) tert-Butyl (±)-trans-4-benzylamino-3-hydroxypiperidine-1-carboxylate

The ester (3b) (13.24 g, 66.5 mmole) was combined with benzylamine (14.53 mL, 133 mmole) and stirred while heating at 115° C. The reaction was allowed to stir for 8 hr at 115° C. and then allowed to cool to ambient temperature. EtOAc was added and the organic layer was washed sequentially with $H_2O$ and saturated NaCl solution. The organic layer was dried over $Na_2SO_4$ and concentrated to yield a yellow solid (19.31 g, 95%): LCMS: m/z 307 (M+H)$^+$. This mixture of regioisomers was chromatographed (preparative HPLC) on Lichrosphere silica gel 60A; 12 u, 100 mm ID×250 mm L; 70:30:0.5 hexanes:THF:diethylamine; 500 ml/min; uv detection 254 nm; 4.5 g mixture per injection. The products, tert-butyl (±)-trans-3-benzylamino-4-hydroxy-piperidine-1-carboxylate and tert-butyl (±)-trans-4-benzylamino-3-hydroxy-piperidine-1-carboxylate, as assigned by NMR, were obtained in a 3:1 ratio with retention times of 8.4 min and 6.5 min, respectively.

(d) tert-Butyl (±)-trans-4-amino-3-hydroxypiperidine-1-carboxylate

A solution of the ester (3c) (0.5 g, 1.63 mmole) in EtOH (40 mL) was treated with 10% palladium on carbon (catalytic) and hydrogenated in a Parr bottle for 6 hr at 40 psi. The solution was filtered through a plug of Celite®, and the filter pad was washed with EtOH. The filtrate was concentrated to yield a yellow oil (0.35 g, 99%). No further purification was required.

MS (ES) m/z 217 (M+H)$^+$.

(e) tert-Butyl (±)-trans-3-Hydroxy-4-[3-oxo-3,4-dihydro-2H-pyrido[3,2-b][1,4]thiazin-6-ylmethyl)amino]piperidine-1-carboxylate A solution of amine (3d) is heated at 85° C. for 2 hours with the carboxaldehyde (2o) in DMF/methanol/acetic acid with 3A molecular sieves, cooled and is treated with an excess of sodium cyanoborohydride. After stirring overnight, the mixture is diluted with chloroform (20 ml) and washed with aqueous $Na_2CO_3$. The organic fraction is dried and evaporated. Chromatography of the residue on silica gel gives the product (f) (±)-trans-3-Hydroxy-4-[3-oxo-3,4-dihydro-2H-pyrido[3,2-b][1,4]thiazin-6-ylmethyl)amino]piperidine A solution of (3e) in $CH_2Cl_2$ is treated with 4.0 N HCl/dioxane. The solution is allowed to stir for 30 min and then is concentrated in vacuo and dissolved in MeOH and treated with MP-Carbonate resin. The solution is then filtered and evaporated to dryness.

(g) Title Compound

A 1:1 mixture of oxirane (2f) and piperidine (3f) is heated at 85° C. for 3 hr and then chromatographed on silica gel to provide the product Example 4

6({(3R,4S)-1-[2-(2,3-Dihydro-[1,4]dioxino[2,3-f]quinolin-10-yl)-ethyl]-3-fluoro-piperidin-4-ylamino}-methyl)-4H-pyrido[3,2-b][1,4]thiazin-3-one

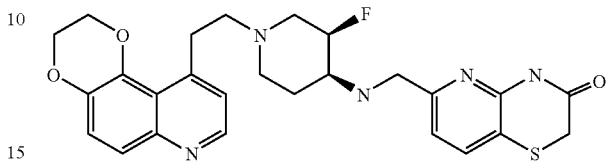

(a) 7-Bromo-2,3-dihydro-benzo[1,4]dioxin-6-ylamine

A solution of 2,3-dihydro-benzo[1,4]dioxin-6-ylamine (1 g, 6.6 mmol) in tetrahydrofuran (15 ml) was cooled to −78 deg C. then treated with 1 drop of concentrated sulphuric acid followed by N-bromosuccinimide (1.2 g, 6.6 mmol). The mixture was allowed to warm to room temperature over 1 hour then evaporated. The residue was dissolved in ether, washed with water then brine, dried and evaporated to afford an oil (1.4 g, 93%).

MS (+ve ion electrospray) m/z 231 (MH+).

(b) 5-[(7-Bromo-2,3-dihydro-benzo[1,4]dioxin-6-ylamino)-methylene]-2,2-dimethyl-[1,3]dioxane-4,6-dione A mixture of aniline (4a) (14.8 g, 64.3 mmol), triethyl orthoformate (12.7 mL, 77.2 mmol) and 2,2-dimethyl-[1,3]dioxane-4,6-dione (Meldrum's acid) (11.1 g, 77.2 mmol) in ethanol (70 mL) was heated to reflux. After 1 hour the mixture was allowed to cool to room temperature then filtered, washing with ethanol then ether, to afford a white solid (22.9 g, 93%).

MS (+ve ion electrospray) m/z 385 (MH+).

(c) 6-Bromo-2,3-dihydro-7H-[1,4]dioxino[2,3-f]quinolin-10-one

Enamine (4b) (22.9 g) was added portionwise to refluxing Dowtherm A (45 mL) over 3 minutes. After a further 3 minutes at reflux the mixture was cooled to room temperature. Ethyl acetate/hexane (10 mL/20 mL) was added and a black solid isolated by filtration. This residue was dissolved in hot methanol (400 mL) and filtered through Keiselguhr. Water (800 mL) was added and the mixture stored at 5° C. overnight. Filtration and drying afforded a pale yellow solid (10.3 g, 61%).

MS (APCI−) m/z 281 [M−H]−

(d) 2,3-Dihydro-7H-[1,4]dioxino[2,3-f]quinolin-10-one

A suspension of (4c) (3.4 g, 12 mmol) in water/dioxan (150 mL/80 mL) was treated with 1M aqueous sodium hydroxide solution then hydrogenated over 10% palladium on charcoal (1.5 g) for 20 hours. The mixture was filtered then acidified with 5M aqueous hydrochloric acid. On concentrating to ca 100 mL, a solid began to crystallise out. The mixture was stored at 5° C. overnight. Filtration and drying afforded a pale yellow solid (2.8 g, 100%).

MS (APCI−) m/z 202 [M−H]−

(e) 10-Bromo-2,3-dihydro-[1,4]dioxino[2,3-f]quinoline

The quinolinone (4d) in dry DMF (8 mL) was cooled in ice and phosphorus tribromide (0.7 mL) added drop-wise, and the mixture was stirred, with ice-cooling for 30 minutes then allowed to warm to room temperature and stirred for a further 2 hours. It was cooled in ice and sodium carbonate solution was added and the solid was collected, washed well with water, and dried in vacuo, to afford a pale yellow solid (1.65 g).

MS (ES) m/z 267 (M+H)+.

(f) 10-Vinyl-2,3-dihydro-[1,4]dioxino[2,3-f]quinoline

To a solution of (4e) (0.8 g) and vinyltributyltin (1.05 mL) in degassed toluene (15 ml) was added tetrakis(triphenylphosphine) palladium (0) (173 mg) and the mixture was refluxed under argon for 2 days. More vinyltributyltin (0.8 mL) and tetrakis(triphenylphosphine) palladium (0) (173 mg) were added and the reaction mixture was heated at 130° C. for a further 18 hours. Evaporation and flash silica chromatography eluting with hexane-DCM and ethyl acetate-DCM afforded the product as a yellow oil (500 mg, 64%).

MS (+ve ion electrospray) m/z 214 (MH+).

(g) {(3R,4S)-1-[2-(2,3-Dihydro-[1,4]dioxino[2,3-f]quinolin-10-yl)-ethyl]-3-fluoro-piperidin-4-yl}-carbamic acid benzyl ester A mixture of (4f) (373 mg), piperidine (2i) (440 mg) and chloroform (3 ml) were heated at 120° C. in a loosely capped vial for 18 hours, under argon. The product was purified by flash silica chromatography eluting with a 0-5% methanol in dichloromethane gradient affording the product as a foam (480 mg, 59%).

MS (+ve ion electrospray) m/z 466 (MH+).

(h) (3R,4S)-1-[2-(2,3-Dihydro-[1,4]dioxino[2,3-f]quinolin-10-yl)-ethyl]-3-fluoro-piperidin-4-ylamine The carbamate (4g) was hydrogenated in methanol at room temperature over 10% palladium charcoal, filtered and evaporated to afford the product (240 mg, 71%)

MS (+ve ion electrospray) m/z 332 (MH+).

(i) Title Compound

A mixture of aldehyde (2o) (142 mg) and amine (4h) (240 mg) in DMF/methane/acetic acid with 3A molecular sieves was heated at 85° C. for 3 hours, cooled and was treated with an excess of sodium cyanoborohydride. After stirring overnight, the mixture was diluted with chloroform (20 ml) and washed with aqueous sodium bicarbonate. The organic fraction was dried and evaporated. Chromatography of the residue on silica gel gave the free base of the title compound (95mg).

¹H NMR δH (DMSO, 400 MHz), 1.29-1.32 (2H, m), 1.66-1.68 (2H, d), 2.07 (2H, t), 2.56 (2H, m), 2.89 (2H, m), 3.20 (3H, m), 3.95 (3H, s), 6.76 (1H, d), 7.20 (1H, s), 7.35 (1H, d), 8.15 (1H, d), 8.72 (1H, s)

MS (+ve ion electrospray) m/z 510 (MH+).

Example 5

6-{[(1-{(2R/S)-2-hydroxy-2-[3-(methyloxy)-5-quinoxalinyl]ethyl}-4-piperidinyl)amino]methyl}-2H-pyrido[3,2-b][1,4]thiazin-3(4H)-one dihydrochloride

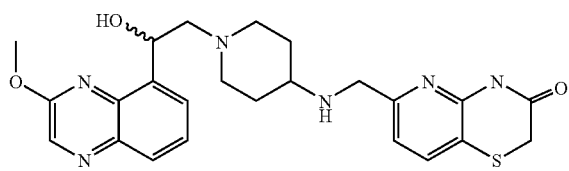

(a) 2-Nitro-6-triisopropylsilanyloxy-phenylamine

A solution of 2-amino-3-nitro-phenol (42.9 g, 278 mmol) and imidazole (28.4 g, 417 mmol) in tetrahydrofuran (750 ml) was treated with chloro-triisopropyl-silane (62.3 g, 323 mmol). After 18 hours the mixture was filtered, diluted with ethyl acetate, washed with water, dried and evaporated to give an oil (91 g).

MS (+ve ion electrospray) m/z 311 (MH+).

(b) 3-Triisopropylsilanyloxy-benzene-1,2-diamine

A solution of (5a) (91 g) in ethanol (500 ml) was hydrogenated over 10% palladium on charcoal (8.5 g) for 3 days then filtered and evaporated to give an oil (80.7 g).

MS (+ve ion electrospray) m/z 281 (MH+).

(c) 8-Triisopropylsilanyloxy-1H-quinoxalin-2-one

A solution of (5b) (80.7 g) in ethanol (1 litre) was treated with a 50% solution of ethyl glyoxalate in toluene (60 ml, 294 mmol) and heated to reflux for 2 hours. The mixture was left at room temperature overnight and filtered affording 5-triisopropylsilanyloxy-1H-quinoxalin-2-one. The filtrate was evaporated and the residue chromatographed eluting with a 0-3% gradient of methanol in dichloromethane affording 8-triisopropylsilanyloxy-1H-quinoxalin-2-one as a white solid (14.9 g).

MS (+ve ion electrospray) m/z 319 (MH+).

(d) 2-Methoxy-8-triisopropylsilanyloxy-quinoxaline

A solution of (5c) (2.0 g, 6.2 mmol) in dichloromethane/methanol/acetonitrile (40 ml/4 ml/40 ml) was treated with triethylamine (1.1 ml, 8 mmol) then a solution of (trimethylsilyl)diazomethane in hexane (2M; 4 ml, 8 mmol). The mixture was stirred overnight then evaporated. The residue was chromatographed on silica eluting with dichloromethane affording an oil (1.0 g, 48%).

MS (+ve ion electrospray) m/z 333 (MH+).

(e) 3-Methoxy-quinoxalin-5-ol

A solution of (5d) (6.95 g, 21 mmol) in tetrahydrofuran/methanol (280 ml/140 ml) was treated with caesium fluoride (4.73 g, 31.4 mmol) and stirred for 18 hours. The mixture was evaporated and the residue partitioned between diethyl ether and dilute aqueous hydrochloric acid. The aqueous phase was further extracted with diethyl ether and the combined extracts dried and evaporated to give an oil (4.2 g).

MS (+ve ion electrospray) m/z 177 (MH+).

(f) 1,1,1-Trifluoro-methanesulfonic acid 3-methoxy-quinoxalin-5-yl ester

A solution of (5e) (4.23 g, 21 mmol) in dichloromethane (35 ml) was treated with triethylamine (4.5 ml, 32.1 mmol) then N-phenyltrifluoromethanesulfonimide (11.4 g, 32 mmol) was added. The mixture was stirred overnight then washed with saturated aqueous sodium carbonate solution. The aqueous phase was further extracted with dichloromethane and the combined organic extracts were dried and evaporated. The residue was chromatographed on silica eluting with 50% hexane in dichloromethane and then dichloromethane, affording an oil (5.6 g, 87%).

MS (+ve ion electrospray) m/z 309 (MH+).

(g) 1-(3-methoxyquinoxalin-5-yl)ethanone

To a solution of triflate (5f) (7.4 g, 24.2 mmol) and 1,3-bis(diphenylphosphino) propane (1.0 g, 0.24 mmol) in DMF (100 mL), under argon, were added palladium acetate (0.55 g, 0.24 mmol), triethylamine (6.73 mL, 48.6 mmol) and butyl vinyl ether (12.6 mL, 97.0 mmol). The reaction mixture was heated at 70° C. for 8.5 hours. DMF was removed in vacuo and the residue was chromatographed on a silica gel column eluting with 0-2% methanol in dichloromethane, affording the product as an oil (4.22 g, 68%)

MS (+ve ion electrospray) m/z 203 (MH+).

(h) 2,2-dibromo-1-[3-(methyloxy)-5-quinoxalinyl]ethanone

To a solution of ethanone (5g) (3.95 g, 19.5 mmol) in dioxan (40 mL), a suspension of bromine (1.14 mL, 22 mmol) in dioxan (40 mL) was added at room temperature. The reaction mixture was stirred at room temperature over 2 nights. The reaction mixture was basified by addition of an aqueous solution of sodium bicarbonate and extracted several times with dichloromethane. The combined organic extracts were washed with an aqueous solution of sodium sulfite, dried over magnesium sulfate and evaporated in vacuo. The residue was chromatographed on a silica gel column eluting with 0-2% methanol in dichloromethane, affording the product as an oil (4.19 g, 59%).

MS (+ve ion electrospray) m/z 361 (MH+).

(i) 2-bromo-1-[3-(methyloxy)-5-quinoxalinyl]ethanone

To a solution of ethanone (5h) (4.19 g, 11.64 mmol) in THF (20 mL), cooled to 0° C., a mixture of diethyl hydrogen phosphite (1.56 mL, 12 mmol), and triethylamine (1.68 mL, 12 mmol) in THF (10 mL) was added slowly. The reaction mixture was allowed to reach room temperature overnight. More diethyl hydrogen phosphite (2×0.08 mL), and triethylamine (2×0.08 mL) were added and the reaction mixture was evaporated in vacuo after 7.5 hours. Water was added to the residue. A solid precipitated out, was washed with water and dried to afford the product as a white powder (2.68 g, 82%).

MS (+ve ion electrospray) m/z 282 (MH+).

(j) (+/−) 2-(methyloxy)-8-(2-oxiranyl)quinoxaline

The ketone (5i) (2.83 g, 10.07 mmol) was partially dissolved in methanol (50 mL). The reaction mixture was cooled down to 0° C. before sodium borohydride (0.78 g, 20.6 mmol) was added portionwise. The reaction mixture was stirred at 0° C. for 1 hour. More sodium borohydride was added (0.14 g) and the new reaction mixture was stirred for a further 20 minutes. Cesium carbonate (7.5 g, 20 mmol) was then added and the reaction mixture was allowed to reach room temperature. Stirring at room temperature was continued for 3 days until total conversion to epoxide. The mixture was diluted with water and extracted several times with dichloromethane. The combined organic extracts were washed with water, dried over magnesium sulfate and evaporated in vacuo. The residue was chromatographed on a silica gel column eluting with 0-1% methanol in dichloromethane, affording the product as a white solid (0.83 g, 41%)

MS (+ve ion electrospray) m/z 203 (MH+).

(k) (+/−) 1,1-dimethylethyl (1-{2-hydroxy-2-[3-(methyloxy)-5-quinoxalinyl]ethyl}-4-piperidinyl)carbamate A mixture of oxirane (5j) (0.83 g, 4.1 mmol) and 1,1-dimethylethyl 4-piperidinylcarbamate (1.23 g, 6.16 mmol) in DMF (1 mL) was heated at 90° C. for 4 hours then cooled down to room temperature. The reaction mixture was diluted with ethyl acetate and washed with water. The aqueous layer was extracted a second time with ethyl acetate. The combined organic extracts were dried over magnesium sulfate and evaporated in vacuo. The residue was chromatographed on a silica gel column eluting with 2-5% methanol in dichloromethane, affording the product as a white solid (1.46 g, 88%)

MS (+ve ion electrospray) m/z 403 (MH+).

(l) (+/−) 2-(4-amino-1-piperidinyl)-1-[3-(methyloxy)-5-quinoxalinyl]ethanol

A solution of amine (5k) in dioxan (10 mL) was treated with 4.0N HCl/dioxan. The solution was allowed to stir at room temperature for 3.5 hours. The reaction mixture was diluted with diethyl ether and filtered. The precipitate was washed with more diethyl ether and dried in vacuo. It was then recrystallised from methanol/dichloromethane. The crystals were redissolved in a minimum amount of water and the solution was basified by addition of sodium bicarbonate. The solution was extracted several times with 10% methanol in dichloromethane. The combined organic extracts were dried over magnesium sulfate, filtered and evaporated in vacuo to afford the product as a solid (0.64 g, 57%)

MS (+ve ion electrospray) m/z 303 (MH+).

(m) Title Compound

A mixture of ethanol (5l) (30 mg, 0.1 mmol) and aldehyde (2o) (19 mg, 0.1 mmol) in chloroform/methanol with 3A molecular sieves was heated at reflux for 5 hours, cooled and was treated with sodium triacetoxyborohydride (42 mg, 0.2 mmol). After stirring for 48 hours at room temperature, the mixture was diluted with chloroform and washed with aqueous sodium bicarbonate. The aqueous layer was extracted again with methanol/dichloromethane. The combined organic fractions were dried and evaporated. Chromatography of the residue on silica gel eluting with 5-10% methanol in dichloromethane gave the free base of the title compound (23 mg, 48%).

¹H NMR δH (CDCl₃, 250 MHz), 1.60-1.91 (2H, m), 2.00-2.16 (2H, m), 2.15-2.20 (1H, m) 2.32-2.84 (6H, m), 3.47 (2H, s), 3.87 (2H, s), 4.05 (3H, s), 5.78 (1H, m), 6.98 (1H, d), 7.55-7.61 (2H, m), 7.91-7.94 (2H, m), 8.48 (1 h, s)

MS (+ve ion electrospray) m/z 481 (MH+).

Treatment with 4M HCl in dioxan, evaporation and trituration with ether afforded the title compound.

The mixture of enantiomers was separated using Supercritical Fluid Chromatography (SFC) on Chiralpak AD stationary phase, eluting with 65% methanol (containing 0.5% isopropylamine) in liquid carbon dioxide. This provided the faster-running enantiomer (61 mg, Retention time=9.4 minutes, alpha D=−91.5 degrees) then the slower-running enantiomer (68 mg, Retention time=19.9 minutes, alpha D=+89.1 degrees).

Example 6

(1R/S)-2-{4-[(2,3-dihydro[1,4]dioxino[2,3-c]pyridin-7-ylmethyl)amino]1-1-piperidinyl}-1-[3-(methyloxy)-5-quinoxalinyl]ethanol dihydrochloride

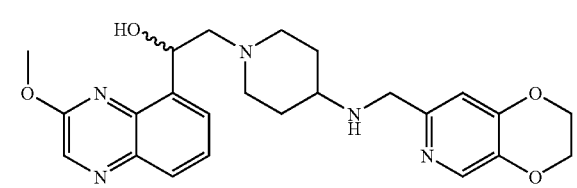

(a) 5-Benzyloxy-2-hydroxymethyl-1 H-pyridin-4-one

A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 mL), and ethanol (20 mL) was heated to reflux overnight. The mixture was allowed to cool to room temperature then filtered. The resultant solid was washed with ether and dried in vacuo (5.9 g).

MS (APCI+) m/z 232 (MH+).

(b) (2,3-Dihydro-[1,4]dioxino[2,3-c]pyridin-7-yl)-methanol

A solution of (6a) (2 g, 8.7 mmol) in water (220 mL) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 mL) then treated with potassium carbonate (2.9 g) and 1,2-dibromoethane (0.6 mL, 7 mmol). The mixture was heated at 85° C. overnight. The cooled mixture was evaporated onto silica and chromatographed eluting with 10-30% methanol in ethyl acetate affording a white solid (250 mg, 21%).

MS (APCI+) m/z 168 (MH+).

(c) 2,3-Dihydro-[1,4]dioxino[2,3-c]pyridine-7-carboxaldehyde

A solution of (6b) (250 mg, 1.5 mmol) in dichloromethane (5 mL) was treated with manganese dioxide (650 mg, 7.5 mmol). After 3 days the mixture was filtered and evaporated affording a white solid (150 mg, 61%).

MS (APCI+) m/z 166 (MH+).

(d) Title Compound

The free base was prepared as in Example 5 from amine (5l) (30 mg, 0.1 mmol) and aldehyde (6c) (16 mg, 0.1 mmol).

$^1$H NMR δH (CDCl$_3$, 250 MHz), 1.43-1.61 (2H, m), 1.90-1.95 (2H, m), 2.15 (1H, m), 2.37-2.94 (6H, m), 3.47 (2H, m), 3.81 (2H, s), 4.05 (3H, s), 4.25-4.35 (4H, m), 5.74-5.79 (1H, m), 6.83 (1H, d), 7.55-7.61 (1H, m), 7.91-7.94 (2H, m), 8.11 (1H, s), 8.48 (1H, s) MS (+ve ion electrospray) m/z 452 (MH+).

Treatment with 4M HCl in dioxan, evaporation and trituration with ether afforded the title compound.

Example 7

{1-[2-(9-Chloro-2,3-dihydro-[1,4]dioxino[2,3-f] quinolin-10-yl)-ethyl]-piperidin-4-yl}-(2,3-dihydro-[1,4]dioxino[2,3-c]pyridin-7-ylmethyl)-amine dihydrochloride

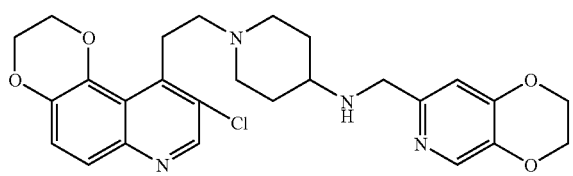

(a) 9-Chloro-2,3-dihydro[1,4]dioxino[2,3-f]quinolin-10 (7H)-one

The quinolone (4d) (5.05 g) in acetic acid (70 mL) was sonicated and warmed until all had dissolved, and then it was treated with N-chlorosuccinimide (3.64 g) and the mixture was heated at 35° C. for 18 hr, cooled and the solid collected and washed with acetic acid and dried in vacuo at 40° C. overnight, to give a white solid (1.65 g)

MS (ES) m/z 238/240 (M+H)$^+$ (b) 10-Bromo-9-chloro-2,3-dihydro-[1,4]dioxino[2,3-f] quinoline The chloroquinolone (7a) in dry DMF (8 mL) was cooled in ice and phosphorus tribromide (0.7 mL) added drop-wise, and the mixture was stirred, with ice-cooling for 30 minutes then allowed to warm to room temperature and stirred for a further 2 hours. It was cooled in ice and sodium carbonate solution was added and the solid was collected, washed well with water, and dried in vacuo, to afford a pale yellow solid (1.65 g).

MS (ES) m/z 301/303 (M+H)$^+$.

(c) 9-Chloro-10-vinyl-2,3-dihydro-[1,4]dioxino[2,3-f] quinoline

The bromide (7b) (1.65 g) in DME (60 mL) under argon, was treated with tetrakis(triphenylphosphine)palladium(0) (0.32 g) and the mixture stirred at room temperature for 20 minutes. Anhydrous potassium carbonate (0.76 g), water (18 mL), and vinylborane:pyridine complex (see F. Kerins and D O'Shea J. Org. Chem. 2002, 67, 4968-4971) was added and the mixture was heated at 100° C. for 2 hr. It was cooled, diluted with water and extracted with ether, dried (magnesium sulfate) and evaporated to dryness. After work-up the product was chromatographed on silica gel, eluting with (methanol-DCM) to afford a white solid (1.35 g).

MS (ES) m/z 248/250 (M+H)$^+$.

(d) {1-[2-(9-Chloro-2,3-dihydro-[1,4]dioxino[2,3-f]quinolin-10-yl)-ethyl]-piperidin-4-yl}-carbamic acid tert-butyl ester A mixture of the vinyl-quinoline (7c) (680 mg) and piperidin-4-yl-carbamic acid tert-butyl ester (815 mg) in DMF (0.9 mL) and tetramethylguanidine (5 drops) was heated at 100° C. for 18 hours. It was cooled, diluted with water and extracted with ethyl acetate, dried (magnesium sulfate) and evaporated to dryness. After work-up the product was chromatographed on silica gel, eluting with methanol-DCM to afford the desired product (0.82 g).

MS (ES) m/z 448 (M+H)$^+$.

(e) 1-[2-(9-Chloro-2,3-dihydro-[1,4]dioxino[2,3-f]quinolin-10-yl)-ethyl]-piperidin-4-ylamine The ester (7d) (0.82 g) in DCM (21 mL) was treated with TFA (21 mL) at room temperature for 1 hr and evaporated. Water and sodium carbonate were added and the solution was extracted with 10% methanol in ethyl acetate, dried (magnesium sulfate) and evaporated to afford the product (0.53 g)

MS (ES) m/z 348 (M+H)$^+$.

(f) Title Compound

The amine (7e) (0.53 g) and aldehyde (6c) (0.25 g) were dissolved in DMF (16 mL) and sodium triacetoxyborohydride (0.96 g) added and the solution was stirred overnight at room temperature. The reaction mixture was quenched with 2N HCl, basified with sodium bicarbonate solution, and extracted with methanol-DCM to afford the free base of the title compound (0.25 g).

$^1$H NMR of the hydrochloride salt δH (d6-DMSO), 9.60 (2H, bs), 8.73 (1H, s), 8.20 (1H, s), 7.60 (1H, d), 7.45 (1H, d), 7.20 (1H, s), 4.50 (2H, m), 4.40 (4H, m), 4.32 (2H, m), 4.25 (2H, m), 3.90-3.70 (3H, m), 3.40-3.10 (6H, m), 2.35-2.05 (4H, m), MS (+ve ion electrospray) m/z 497 (MH+).

This material, as a solution in chloroform/methanol, was treated with an excess of 1M HCl in ether and evaporated to dryness. The solid was triturated under ether, filtered and dried under vacuum to provide the title compound (0.33 g).

Example 8

6-{[(1-{2-hydroxy-2-[2-(methyloxy)-8-quinolinyl]ethyl}4-piperidinyl)amino]methyl}-2H-pyrido[3,2-b][1,4]oxazin-3(4H)-one

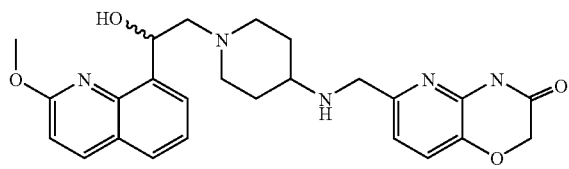

(a) 8-(1-Butoxy-vinyl)-2-methoxy-quinoline

Triflate (2c) (2.50 g, 8.14 mmol) was dissolved in DMF (25 mL). After subsequent addition of butyl vinyl ether (4.21 mL, 32.55 mmol), palladium acetate (0.182 g, 0.81 mmol), 1,3-bis(diphenylphosphino)propane (0.334 g, 0.81 mmol), and N,N-diisopropylethylamine (4.25 mL, 24.4 mmol), the reaction was heated to 60° C. and stirred for 18 hours. The solution was then cooled to ambient temperature and poured into a saturated NaHCO₃ solution. The solution was then extracted with EtOAc and washed with water (3×). The organic layer was then dried over Na₂SO₄, filtered, and the solvent removed under reduced pressure yielding an oil (2.80 g, >100% crude)[1].

MS (+ve ion electrospray) m/z 258 (MH+).

(b) 2-Bromo-1-(2-methoxy-quinolin-8-yl)-ethanone

Vinyl (8a) (2.42 g, 9.42 mmol) was dissolved in THF (30 mL). Water (10 mL) was added followed by N-bromosuccinimide (1.84 g, 10.36 mmol) at ambient temperature. Immediately after addition, the color changed to a lighter color. The reaction was stirred 10 minutes, filtered, and the solvent removed under reduced pressure. This was chromatographed on silica gel (CH₂Cl₂) to yield a yellow solid (1.25 g, 47%).

MS (+ve ion electrospray) m/z 280 (MH+).

(c) {1-[2-(2-Methoxy-quinolin-8-yl)-2-oxo-ethyl]-piperidin-4-yl}-carbamic acid tert-butyl ester.

Piperidin-4-yl-carbamic acid tert-butyl ester (0.356 g, 1.78 mmol) was dissolved in dichloromethane (5.0 mL). Triethylamine (0.52 mL, 3.75 mmol) was added and the solution stirred for 15 minutes at ambient temperature. In a separate flask, bromomethyl (8b) (0.50 g, 1.78 mmol) was dissolved in dichloromethane (5.0 mL), and then added to the original solution. The reaction mixture was allowed to stir at ambient temperature for 18 hours. The solution was then diluted with ethyl acetate and washed with water and saturated aqueous NaCl solution. The organic layer was then dried over Na₂SO₄, filtered, and the solvent removed under reduced pressure. The reaction yielded an off-white solid (0.501 g, 70%).

MS (+ve ion electrospray) m/z 400 (MH+).

(d) {1-[2-Hydroxy-2-(2-methoxy-quinolin-8-yl)-ethyl]-piperidin-4-yl}-carbamic acid tert-butyl ester The ketone (8c) (0.25 g, 0.627 mmol) was dissolved in tetrahydrofuran (10 mL) and the solution cooled to 0° C. NaBH₄ (0.024 g, 0.627 mmol) was added and the solution stirred at 0° C. for 2 hours and allowed to warm to ambient temperature overnight. The reaction was not complete, and thus another equivalent of NaBH₄ (0.024 g, 0.627 mmol) was added at 0° C. The solution was allowed to warm to ambient temperature and was stirred for 3 more hours. The reaction was quenched with saturated NaHCO₃ solution and diluted with ethyl acetate. The organic layer was washed with water and saturated aqueous NaCl solution, dried over Na₂SO₄, filtered, and the solvent removed under reduced pressure. Purification by flash chromatography (silica gel, acetone/chloroform) yielded an off-white solid (0.162 g, 65%).

MS (+ve ion electrospray) m/z 402.4 (MH+).

(e) (4-Amino-piperidin-1-yl)-1-(2-methoxy-quinolin-8-yl)-ethanol

The carbamate (8d) (0.158 g, 0.394 mmol) was dissolved in dichloromethane (2 mL). HCl in dioxane (1.0M:5 mL:5 mmol) was added and the solution allowed to stir at room temperature for 18 hours. The solvent and excess HCl were removed under reduced pressure, yielding the di-HCl salt (0.144 g, 98%) as a yellow solid.

MS (+ve ion electrospray) m/z 302.4 (MH+).

(f) Title Compound

Amine (8e) (0.144 g, 0.482 mmol) was added to aldehyde (1j) (0.094 g, 0.530 mmol) dissolved in CH₂Cl₂ (3 mL) and MeOH (3 mL). NaHCO₃ (0.202 g, 2.41 mmol) was then added and the solution allowed to stir at ambient temperature for 17 hours. The solution was cooled to 0° C., excess sodium borohydride was added, and it was allowed to stir at ambient temperature for 4 hours. The reaction mixture was poured into a saturated solution of NaHCO₃ and extracted with CHCl₃. (3×). The organic layer was washed with water (2×) and brine, dried over Na₂SO₄, and evaporated to yield a yellow oil. This was chromatographed on silica gel (90:10:1 CHCl₃/MeOH/NH₄OH) to yield an off-white solid (0.012 g, 5%).

[1]¹H NMR (400 MHz, CDCl₃) δ 7.98 (d, 1H), 7.84 (d, 1H), 7.62 (d, 1H), 7.39 (t, 1H), 7.20 (d, 1H), 6.94 (d, 1H), 6.89 (d, 1H), 5.77 (dd, 1H), 4.63 (s, 3H), 4.02 (s, 3H), 3.84 (s, 2H), 3.15 (d, 1H), 3.01 (d, 1H), 2.59 (m, 2H), 2.38 (m, 1H), 2.21 (m, 1H); 1.97 (m, 2H); 1.58 (m, 2H). MS (+ve ion electrospray) m/z 464.4 (MH+). -

Example 9

6-[({1-[2-(4-quinolinyl)ethyl]-4-piperidinyl}amino)methyl]-2H-pyrido[3,2-b][1,4]thiazin-3(4H)-one dihydrochloride

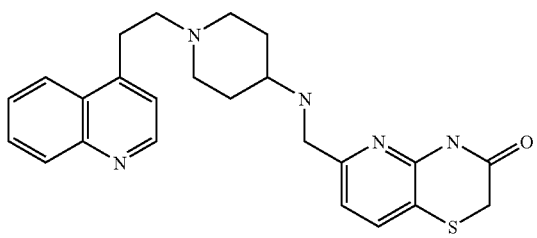

(a) 1,1-dimethylethyl {1-[2-(4-quinolinyl)ethyl]-4-piperidinyl}carbamate

A solution of lepidine (2.5 mmol, 0.33 mL), 1,1-dimethylethyl 4-piperidinylcarbamate (2.5 mmol, 0.500 g), 37% aqueous formaldehyde (2.6 mmol, 0.20 mL), and 6N HCl (2.6 mmol, 0.44 mL) in ethanol (1 mL) was heated to 50° C. overnight. The reaction mixture was cooled, diluted with chloroform, and washed with aqueous sodium bicarbonate solution. The aqueous layer was removed and the organic layer was washed with water and brine, dried over magnesium sulfate, filtered, concentrated and chromatographed in 90:10:1 chloroform:methanol:ammonium hydroxide to afford the product as a white solid (278 mg, 31%).

LC-MS m/z 356 (MH+)

(b) 1-[2-(4-quinolinyl)ethyl]-4-piperidinamine trihydrochloride 1,1-dimethylethyl {1-[2-(4-quinolinyl)ethyl]-4-piperidinyl}carbamate (9a) (278 mg) was dissolved in chloroform and diluted with 4N HCl in dioxane solution. After stirring two hours, the reaction mixture was evaporated to dryness to afford the product as a solid (180 mg, 100%).

LC-MS m/z 286 (MH+)

(c) Title Compound

The trihydrochloride salt of amine (9b) (0.36 mmol, 180 mg) was dissolved in 3 mL of 1:1 dichloromethane:methanol and treated with sodium bicarbonate (1.8 mmol, 152 mg) and carbaldehyde (2o) (0.36 mmol, 70 mg) and stirred overnight. The suspension was treated with sodium triacetoxyborohydride (0.54 mmol, 114 mg) and stirred overnight. The resulting reaction mixture was diluted with dichloromethane and poured into saturated aqueous sodium bicarbonate. The aqueous layer was extracted with dichloromethane, and the combined organic layers were washed with water and brine, dried over magnesium sulfate, filtered, concentrated, and chromatographed in 90:10:1 chloroform:methanol:ammonium hydroxide. The final product was obtained in 34% yield, 52 mg and converted to dihydrochloride salt.

δH (CDCl$_3$, 400 MHz), 8.81 (d, 1H), 8.11 (d, 1H), 8.09 (bs, 1H), 8.06(d, 1H), 7.70 (t, 1H), 7.63-7.55 (m, 2H), 7.28 (s, 1H), 6.99 (d, 1H), 3.85 (s, 2H), 3.43 (s, 2H), 3.28 (t, 2H), 3.04 (m, 2H), 2.73 (t, 2H), 2.56 (m, 1H), 2.17 (m, 1H), 1.95 (m, 1H), 1.64-1.52 (m, 2H)

MS (ES) m/e 434 (M+H)$^+$.

Example 10

4-[2-(3-hydroxy-4-{[(3-oxo-3,4-dihydro-2H-pyrido[3,2-b][1,4]oxazin-6-yl)methyl]amino}-1-piperidinyl)ethyl]-6-quinolinecarbonitrile dihydrochloride (isomer E2)

(a) cis-4-tert-Butoxycarbonylamino-3-hydroxy-piperidine-1-carboxylic acid benzyl ester. Racemic cis-4-tert-butoxycarbonylamino-3-hydroxy-piperidine-1-carboxylic acid benzyl ester was prepared according to the procedure outlined by Kim et al. [Syn. Comm. 2001, 31, 1081-1089] starting from 3,6-dihydro-2H-pyridine-1-carboxylic acid benzyl ester.

MS (ES) m/z 351 (M+H)$^+$.

(b) cis-4-tert-Butoxycarbonylamino-3-hydroxy-piperidine-1-carboxylic acid benzyl ester enantiomer 1 and cis-4-tert-Butoxycarbonylamino-3-hydroxy-piperidine-1-carboxylic acid benzyl ester enantiomer 2

71.0 g of the racemate (10a) was dissolved in methanol (710 mL) and resolved through multiple injections (1×8 g substrate injection; 5×10 g substrate injection; 1×7 g substrate injection; and 1×6 g substrate injection) on a Chiralpak AD column (77×250 mm) eluting with 100% methanol at a flow rate of 280 mL/minute with UV detection at 254 nm. 31.15 g of cis-4-tert-butoxycarbonylamino-3-hydroxy-piperidine-1-carboxylic acid benzyl ester fast running isomer (>99% ee, retention time 3.8 minutes (sharp), designated Isomer 1) and 26.75 g of cis-4-tert-butoxycarbonylamino-3-hydroxy-piperidine-1-carboxylic acid benzyl ester slow running isomer (>99% ee, retention time 8.0 minutes (very broad), designated Isomer 2) were obtained.

(c) cis-(3-Hydroxy-piperidin-4-yl)-carbamic acid tert-butyl ester isomer 2

10.0 g of cis-4-tert-Butoxycarbonylamino-3-hydroxy-piperidine-1-carboxylic acid benzyl ester slow running Isomer 2 (10b), was dissolved in methanol (350 mL) and was degassed. Pearlman's catalyst (palladium hydroxide on carbon, 20wt % Pd (dry basis), ≦50% water, 500 mg) was added and the mixture was purged with hydrogen and stirring continued under a balloon of hydrogen for 12 hours. The mixture was degassed with argon, filtered through a pad of Celite, and evaporated to dryness to afford 6.2 g (100%) of a white solid.

MS (ES) m/z 217 (M+H)$^+$.

(d) 1,1-dimethylethyl {(3R,4S)-1-[2-(6-cyano-4-quinolinyl)ethyl]-3-hydroxy-4-piperidinyl}carbamate A mixture of the vinyl-quinoline (1d) and piperidine (10c) was treated as in example (7d) to afford the desired product in 86% yield.

MS (ES) m/z 397 (M+H)$^+$.

(e) 4-{2-[(3R,4S)-4-amino-3-hydroxy-1-piperidinyl]ethyl}-6-quinolinecarbonitrile dihydrochloride The carbamate (10d) was dissolved in dichloromethane. 4M HCl in dioxane was added and the solution allowed to stir at room temperature for 18 hours. The solvent and excess HCl were removed under reduced pressure, yielding the di-HCl salt as a yellow solid.

MS (+ve ion electrospray) m/z 297 (MH+).

(f) Title Compound

The dihydrochloride salt (10e) (1.4 mmol, 650 mg) was dissolved in 3 mL methanol and diluted with 9 mL dichloromethane. The solution was treated with triethylamine (7.1 mmol, 0.99 mL) and aldehyde (1j) (1.4 mmol, 253 mg) and stirred overnight. The resulting solution was treated with sodium borohydride (1.4 mmol, 54 mg) and stirred two hours. The reaction mixture was diluted with chloroform and poured into saturated aqueous sodium bicarbonate solution. The aqueous layer was extracted with chloroform, and the combined organic layers were washed with brine, dried over magnesium sulfate, filtered, concentrated, and chromatographed in 90:10:1 chloroform:methanol:ammonium hydroxide to afford the product a solid (394 mg, 60%).

δH (DMSO, 400 MHz), 8.94 (d, 1H), 8.81 (d, 1H), 8.15 (d, 1H), 8.05 (d, 1H), 7.58 (t, 1H), 7.30 (d, 1H), 7.02 (d, 1H), 4.61 (s, 2H), 4.43 (bs, 1H), 3.70 (m, 3H), 3.29 (t, 2H), 2.66 (t, 3H), 2.60 (bs, 1H), 2.39 (m, 1H), 2.28 (m, 1H), 2.00 (m, 1H), 1.66 (m, 1H), 1.52 (m, 1H) (+ve ion electrospray) m/z 459 (MH+).

Example 11

4-[2-(3-hydroxy-4-{[[(3-oxo-3,4-dihydro-2H-pyrido[3,2-b][1,4]thiazin-6-yl)methyl]amino}-1-piperidinyl)ethyl]-6-quinolinecarbonitrile dihydrochloride (E2 isomer)

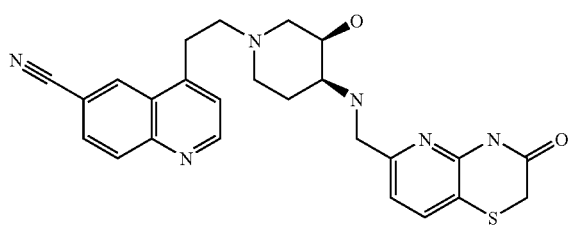

(a) Title Compound

Dihydrochloride (10e) (1.4 mmol, 650 mg) was dissolved in 3 mL methanol and diluted with 9 mL dichloromethane. The solution was treated with triethylamine (7.1 mmol, 0.99 mL) and aldehyde (2o) (1.4 mmol, 345 mg, at 80% purity) and stirred overnight. The resulting solution was treated with sodium borohydride (1.4 mmol, 54 mg) and stirred two hours. The reaction mixture was diluted with chloroform and poured into saturated aqueous sodium bicarbonate solution. The aqueous layer was extracted with chloroform, and the combined organic layers were washed with brine, dried over magnesium sulfate, filtered, concentrated, and chromatographed in 90:10:1 chloroform:methanol:ammonium hydroxide to afford the product as a solid (405 mg, 60%).

δH (DMSO, 400 MHz), 10.91 (bs, 1H), 8.94 (d, 1H), 8.81 (d, 1H), 8.15 (d, 1H), 8.04 (d, 1H), 7.73 (d, 1H), 7.58 (d, 1H), 7.10 (d, 1H), 4.43 (bs, 1H), 3.72 (m, 3H), 3.53 (s, 1H), 3.28 (t, 2H), 3.17 (d, 1H), 2.66 (t, 1H), 2.60 (bs, 1H), 2.39 (m, 1H), 2.27 (m, 1H), 2.06 (m, 1H), 1.66 (m, 1H), 1.52 (m, 1H) MS (+ve ion electrospray) m/z 475 (MH+).

This material was converted to the dihydrochloride salt by the procedure of example (2p)

Example 12

4-[2-(3-hydroxy-4-{[[(3-oxo-3,4-dihydro-2H-pyrido[3,2-b][1,4]oxazin-6-yl)methyl]amino}-1-piperidinyl)ethyl]-6-quinolinecarbonitrile (E1 isomer)

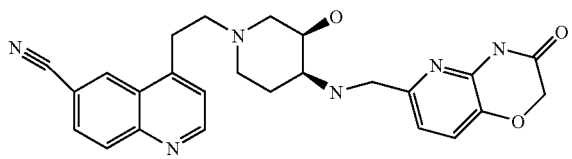

(a) Title Compound

Carbonitrile dihydrochloride (10e) (492 mg, 1.48 mmole), aldehyde (1j) (264 mg, 1.48 mmole) and triethylamine(1.03 mL, 7.42 mmole) were combined in a 1:1 mixture of dichloromethane and methanol (20 mL), and the mixture was stirred for 3 hours. Sodium borohydride (56 mg, 1.48 mmole) were added, and the reaction was stirred at room temperature for 30 minutes. The solution was diluted with chloroform, then washed with saturated aqueous sodium bicarbonate solution and brine. The organic layer was dried over Na₂SO₄ and concentrated in vacuo to yield an off-white solid. This was flash chromatographed on silica gel (90:10:1 CHCl₃/MeOH/NH₄OH) to yield the title compound (450 mg, 57%) as a white solid.

¹H NMR (400 MHz, DMSO) δ 8.96 (d, 1H), 8.79 (s, 1H), 8.31 (s, 1H), 8.17 (d, 1H), 8.08 (d, 1H), 7.70 (d, 1H), 7.55 (s, 1H), 7.01 (d, 1H), 4.60 (s, 2H), 4.45 (m, 1H), 3.76-3.80 (m, 3H), 3.24-3.37 (m, 2H), 2.59-2.79 (m, 4H), 2.40-2.50 (m, 1H), 2.20-2.35 (m, 1H), 1.65-1.78 (m, 1H), 1.42-1.60 (m, 1H), 1.00-1.13 (m, 2H) MS (ES) m/e 459.5 (M+H)⁺.

This material was converted to the dihydrochloride salt by the procedure of example (2p)

Example 13

4-[2-(3-hydroxy-4-{[[(3-oxo-3,4-dihydro-2H-pyrido[3,2-b][1,4]thiazin-6-yl)methyl]amino}-1-piperidinyl)ethyl]-6-quinolinecarbonitrile (E1 isomer)

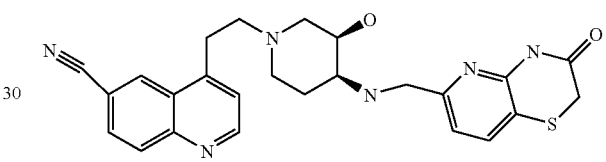

(a) Title Compound

Carbonitrile dihydrochloride (10e) (492 mg, 1.48 mmole), aldehyde (2o) (287 mg, 1.48 mmole) and triethylamine(1.03 mL, 7.42 mmole) were combined in a 1:1 mixture of dichloromethane and methanol (20 mL), and the mixture was stirred for 3 hours. Sodium borohydride (56 mg, 1.48 mmole) were added, and the reaction was stirred at room temperature for 30 minutes. The reaction was diluted with chloroform, then washed with saturated aqueous sodium bicarbonate solution and brine. The organic layer was dried over Na₂SO₄ and concentrated in vacuo to yield an off-white solid. This was flash chromatographed on silica gel (90:10:1 CHCl₃/MeOH/NH₄OH) to yield the title compound (230 mg, 28%) as a white solid.

¹H NMR (400 MHz, DMSO)δ10.91 (s, 1H), 8.95 (d, 1H), 8.81 (s, 1H), 8.32 (s, 1H), 8.15 (d, 1H), 8.04 (d, 1H), 7.74 (d, 1H), 7.59 (s, 1H), 7.10 (d, 1H), 4.45 (m, 1H), 3.70-3.78 (s, 3H), 3.51 (s, 2H), 3.28-3.34 (m, 2H), 2.66-2.79 (m, 4H), 2.42-2.50 (m, 1H), 2.25-2.35 (m, 1H), 1.68-1.80 (m, 1H), 1.43-1.60 (m, 1H), 1.08-1.13 (m, 2H) MS (ES) m/e 475.5 (M+H)⁺.

This material was converted to the dihydrochloride salt by the procedure of example (2p)

Biological Activity

The MIC (μg/ml) of test compounds against various organisms was determined including: *S. epidermidis* CL7, *S. aureus* WCUH29, *S. pneumoniae* 1629, *S. pyogenes* CN10, *H. influenzae* ATCC 49247, *E. faecalis* 2, *M. catarrhalis* Ravasio, *E. coli* 7623. Examples 1, 5, 6, 7, 8, 11, 13 have an MIC≦2 μg/ml versus all these organisms. Examples 4, 10, 12 have an MIC≦16 μg/ml versus all these organisms. Example 9 has an MIC≦16 μg/ml versus some of these organisms.

The invention claimed is:
1. A compound of formula (I) or a pharmaceutically acceptable derivative thereof:

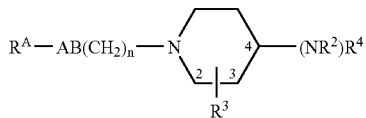

wherein:
$R^A$ is an optionally substituted bicyclic heterocyclic ring system selected from quinolin-4-yl, isoquinolin-5-yl, quinolin-8-yl, thieno[3,2-b]pyridin-7-yl, 2,3-dihydro-[1,4]dioxino[2,3-b]pyridin-8-yl, quinoxalin-5-yl, isoquinolin-8-yl, [1.6]-naphthyridin-4-yl, 1,2,3,4-tetrahydroquinoxalin-5-yl or 1,2-dihydroisoquinoline-8-yl wherein each ring is independently C-substituted with 0-3 groups $R^1$ and/or $R^{1a}$;

$R^1$ and $R^{1a}$ are independently hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted$(C_{1-6})$ alkyl; hydroxy $(C_{1-6})$ alkyl; halogen; $(C_{1-6})$alkyl; $(C_{1-6})$alkylthio; trifluoromethyl; trifluoromethoxy; cyano; carboxy; nitro; azido; acyl; acyloxy; acylthio; $(C_{1-6})$ alkylsulphonyl; $(C_{1-6})$ alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when $Z^3$ and the adjacent atom are $CR^1$ and $CR^{1a}$, $R^1$ and $R^{1a}$ may together represent $(C_{1-2})$alkylenedioxy; provided that $R^1$ and $R^{1a}$, on the same carbon atom are not both optionally substituted hydroxy or amino;
provided that
(i) when $R^A$ is optionally substituted quinolin-4-yl:
it is unsubstituted in the 6-position; or
it is substituted by at least one hydroxy $(C_{1-6})$alkyl, cyano or carboxy group at the 2-, 5-, 6-, 7- or 8-position;

$R^2$ is hydrogen, or $(C_{1-4})$alkyl or $(C_{2-4})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$ alkyl, aminocarbonyl$(C_{1-4})$alkyl, $(C_{2-4})$alkenyl, $(C_{1-4})$ alkylsulphonyl, trifluoromethylsulphonyl, $(C_{2-4})$ alkenylsulphonyl, $(C_{1-4})$alkoxycarbonyl, $(C_{1-4})$ alkylcarbonyl, $(C_{2-4})$alkenyloxycarbonyl or $(C_{2-4})$ alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$ alkoxycarbonyl, $(C_{1-4})$alkylcarbonyl, $(C_{2-4})$alkenyloxycarbonyl, $(C_{2-4})$alkenylcarbonyl; oxo; $(C_{1-4})$ alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or
$R^3$ is in the 2-, 3- or 4-position and is:
trifluoromethyl; carboxy; $(C_{1-6})$alkoxycarbonyl; $(C_{2-6})$ alkenyloxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$ alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the substituents listed above for $R^3$ and/or 0 to 2 groups $R^{12}$ independently selected from:
halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$ alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$ alkyl, hydroxy$(C_{1-6})$alkyl, aminocarbonyl$(C_{1-6})$ alkyl, $(C_{2-6})$alkenyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl $(C_{1-6})$ alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or $R^3$ is in the 2-position and is oxo; or
$R^3$ is in the 3-position and is fluorine, amino optionally substituted by a group selected from hydroxy, $(C_{1-6})$ alkylsulphonyl, trifluoromethylsulphonyl, $(C_{2-6})$alkenylsulphonyl, $(C_{1-6})$alkylcarbonyl, $(C_{2-6})$alkenylcarbonyl, $(C_{1-6})$alkoxycarbonyl, $(C_{2-6})$ alkenyloxycarbonyl, $(C_{1-6})$alkyl and $(C_{2-6})$alkenyl, wherein a $(C_{1-6})$alkyl or $(C_{2-6})$alkenyl moiety may be optionally substituted with up to 2 groups $R^{12}$, or hydroxy optionally substituted as described above for $R^{12}$ hydroxy; in addition when $R^3$ is disubstituted with a hydroxy or amino containing substituent and carboxy containing substituent these may together form a cyclic ester or amide linkage, respectively;

$R^4$ is a group —U—$R^5$ where
U is selected from CO, $SO_2$ and $CH_2$ and
$R^5$ is an optionally substituted bicyclic heterocyclic ring system (A):

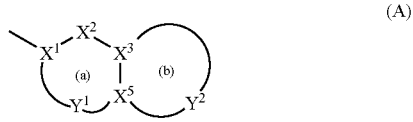

(A)

wherein:
$X^3$ and $X^5$ are C;
ring (a) is optionally substituted pyrido in which $X^1$ is C, $X^2$ is N, and $Y^1$ is a 2 atom linker group each atom of which is independently selected from $CR^{14}$; and
ring (b) is non-aromatic, $Y^2$ is a 4 atom linker group wherein $S(O)_x$ is bonded to $X^5$, $NR^{13}$ is bonded via N to $X^3$ and the other atoms are independently selected from $CR^{14}R^{15}$;
each of $R^{14}$ and $R^{15}$ is independently selected from: H; $(C_{1-4})$alkylthio; halo; carboxy$(C_{1-4})$alkyl; halo$(C_{1-4})$ alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$ alkyl; hydroxy; hydroxy$(C_{1-4})$alkyl; mercapto$(C_{1-4})$ alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; aryl$(C_{1-4})$alkoxy or
$R^{14}$ and $R^{15}$ may together represent oxo;
each $R^{13}$ is independently H; trifluoromethyl; $(C_{1-4})$ alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$ alkenyloxycarbonyl, $(C_{2-4})$alkenylcarbonyl, $(C_{1-4})$ alkyl or $(C_{2-4})$alkenyl and optionally further substituted by $(C_{1-4})$alkyl or $(C_{2-4})$alkenyl;
each x is independently 0, 1 or 2;
n is 0 and AB is $NR^{11}CO$, $CO—CR^8R^9$, $CR^6R^7$—CO, $NHR^{11}SO_2$, $CR^6R^7$—$SO_2$ or $CR^6R^7$—$CR^8R^9$, provided that $R^8$ and $R^9$ are not optionally substituted hydroxy or amino and $R^6$ and $R^8$ do not represent a bond;
or n is 1 and AB is $NR^{11}CO$, $CO—CR^8R^9$, $CR^6R^7$—CO, $NR^{11}SO_2$, $CONR^{11}$, $CR^6R^7$—$CR^8R^9$, O—$CR^8R^9$ or $NR^{11}$—$CR^8R^9$;
provided that $R^6$ and $R^7$, and $R^8$ and $R^9$ are not both optionally substituted hydroxy or amino;
and wherein:
each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$ alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;
or $R^6$ and $R^8$ together represent a bond and $R^7$ and $R^9$ are as above defined;
$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$ alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; and
$R^{11}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;
or where one of $R^3$ and $R^6$, $R^7$, $R^8$ or $R^9$ contains a carboxy group and the other contains a hydroxy or amino group they may together form a cyclic ester or amide linkage.

2. A compound according to claim 1 wherein $R^4$ is optionally substituted isoquinolin-5-yl, quinolin-8-yl, thieno[3,2-b] pyridin-7-yl, 2,3-dihydro-[1,4]dioxino[2,3-b]pyridin-8-yl, quinoxalin-5-yl, isoquinolin-8-yl, [1,6]-naphthyridin-4-yl, 1,2,3,4-tetrahydroquinoxalin-5-yl or 1,2-dihydroisoquinoline-8-yl.

3. A compound according to claim 1 wherein $R^1$ is H, methoxy, methyl, cyano or halogen and $R^{1a}$ is H.

4. A compound according to claim 1 wherein $R^3$ is hydrogen; optionally substituted hydroxy; optionally substituted amino; halogen; $(C_{1-4})$alkoxycarbonyl; $CONH_2$; 1-hydroxyalkyl; $CH_2CO_2H$; $CH_2CONH_2$; —$CONHCH_2$ $CONH_2$; 1,2-dihydroxyalkyl; $CH_2CN$; 2-oxo-oxazolidin-5-yl; or 2-oxo-oxazolidin-5-yl$(C_{1-4}$alkyl).

5. A compound according to claim 1 wherein n is 0 and A and B are both $CH_2$, A is CHOH and B is $CH_2$ or A is NH and B is CO.

6. A compound according to claim 1 wherein —U— is —$CH_2$—.

7. A compound according to claim 1 wherein $Y^2$ has a group S bonded to $X^5$ and a group NHCO bonded via N to to $X^3$.

8. A compound according to claim 1 wherein $R^5$ is 3-oxo-3,4-dihydro-2H-pyrido[3,2-b][1,4]thiazin-6-yl.

9. A compound selected from:
6-({(3R,4S)-3-Fluoro-1-[(R)-2-hydroxy-2-(2-methoxy-quinolin-8-yl)-ethyl]-piperidin-4-ylamino }-methyl)-4H-pyrido[3,2-b][1,4]thiazin-3-one;
6-({(3S,4R)-3-Fluoro-1-[(R)-2-hydroxy-2-(2-methoxy-quinolin-8-yl)-ethyl]-piperidin-4-ylamino }-methyl)-4H-pyrido[3,2-b][1,4]thiazin-3-one;
6-({(3R,4R)-3-Hydroxy-1-[(R)-2-hydroxy-2-(2-methoxy-quinolin-8-yl)-ethyl]-piperidin-4-ylamino }-methyl)-4H-pyrido[3,2-b][1,4]thiazin-3-one;
6-({(3S,4S)-3-Hydroxy-1-[(R)-2-hydroxy-2-(2-methoxy-quinolin-8-yl)-ethyl]-piperidin-4-ylamino }-methyl)-4H-pyrido[3,2-b][1,4]thiazin-3-one;
6-{[(1-{(2R/S)-2-hydroxy-2-[3-(methyloxy)-5-quinoxalinyl]ethyl}-4-piperidinyl )amino]methyl}-2H-pyrido[3,2-b][1,4]thiazin-3(4H)-one;
6-[({1-[2-(4-quinolinyl)ethyl]-4-piperidinyl}amino)methyl]-2H-pyrido[3,2-b][1,4]thiazin-3 (4H)-one; and
4-[2-(3-hydroxy-4-{[(3-oxo-3,4-dihydro-2H-pyrido[3,2-b][1,4]thiazin-6-yl) methyl]amino}-1-piperidinyl) ethyl]-6-quinolinecarbonitrile;
or a pharmaceutically acceptable derivative thereof.

10. A method of treatment of bacterial infections in mammals, which method comprises the administration to a mammal in need of such treatment an effective amount of a compound according to claim 1.

11. A pharmaceutical composition comprising a compound according to claim 1, and a pharmaceutically acceptable carrier.

12. A compound according to claim 1 wherein $R^A$ is unsubstituted quinolin-4-yl, or quinolin-4-yl substituted by a cyano in the 6-position.

13. A compound according to claim 1 wherein $R^A$ is optionally substituted quinolin-8-yl.

14. A compound according to claim 1 wherein $R^A$ is optionally substituted quinoxalin-5-yl.

15. A method of treatment of bacterial infections in mammals, which method comprises the administration to a mammal in need of such treatment an effective amount of a compound according to claim 9.

16. A pharmaceutical composition comprising a compound according to claim 9, and a pharmaceutically acceptable carrier.

\* \* \* \* \*